US008455710B2

(12) United States Patent
Flick

(10) Patent No.: US 8,455,710 B2
(45) Date of Patent: Jun. 4, 2013

(54) CONDUCTIVE WOUND DRESSINGS AND METHODS OF USE

(75) Inventor: A. Bart Flick, Lakemont, GA (US)

(73) Assignee: Argentum Medical, LLC, Chicago, IL (US)

( * ) Notice: Subject to any disclaimer, the term of this patent is extended or adjusted under 35 U.S.C. 154(b) by 134 days.

(21) Appl. No.: 10/421,370

(22) Filed: Apr. 23, 2003

(65) Prior Publication Data

US 2004/0030276 A1   Feb. 12, 2004

Related U.S. Application Data

(63) Continuation of application No. 09/531,245, filed on Mar. 21, 2000, now Pat. No. 6,861,570, which is a continuation of application No. PCT/US98/19689, filed on Sep. 22, 1998, which is a continuation-in-part of application No. 08/935,026, filed on Sep. 22, 1997, now Pat. No. 6,087,549.

(60) Provisional application No. 60/374,769, filed on Apr. 23, 2002.

(51) Int. Cl.
*A61F 13/00* (2006.01)
*A61F 13/15* (2006.01)
*A61F 13/53* (2006.01)

(52) U.S. Cl.
CPC ............... *A61F 13/00* (2013.01); *A61F 13/15* (2013.01)
USPC ...... 604/367; 604/385.01; 604/371; 604/378; 604/355; 602/41; 602/42; 602/43; 602/46; 602/48

(58) Field of Classification Search
USPC ..................... 604/20, 289; 602/41–59; 600/9, 600/15; 601/15; 606/32–41; 607/2, 46, 50, 607/115; 128/888; 424/443–449; 428/411.1
See application file for complete search history.

(56) References Cited

U.S. PATENT DOCUMENTS

| 1,498,059 A | 6/1924 | Tyler |
| 1,545,413 A | 7/1925 | Elmvall |
| 1,975,518 A | 10/1934 | Rose |
| 1,989,282 A | 1/1935 | Kimble et al. |
| 2,577,945 A | 12/1951 | Atherton |

(Continued)

FOREIGN PATENT DOCUMENTS

| DE | 1161384 | 1/1964 |
| EP | 0 099 758 | 2/1984 |

(Continued)

OTHER PUBLICATIONS

Online encyclopedia article "Ripstop nylon" accessed May 27, 2009. http://en.wikipedia.org/wiki/Ripstop_nylon.*

(Continued)

*Primary Examiner* — Tatyana Zalukaeva
*Assistant Examiner* — Adam Marcetich
(74) *Attorney, Agent, or Firm* — Pabst Patent Group LLP

(57) ABSTRACT

Wound treatment dressings comprising combinations of at least one conductive layer, at least one absorbent layer or a moisture regulation layer, and methods of making and methods of use are disclosed for treatment of wounds in humans and animals. The novel dressings aid in healing by helping restore the transepithelial potential of the skin, providing a functional anti-microbial barrier, and allowing for regulation of the moisture content of the wound without disturbing the wound.

21 Claims, 11 Drawing Sheets

U.S. PATENT DOCUMENTS

| | | | | |
|---|---|---|---|---|
| 2,934,066 | A | * | 4/1960 | Stowasser .................. 602/43 |
| 2,943,627 | A | | 7/1960 | Howell |
| 3,326,213 | A | | 6/1967 | Gallagher |
| 3,420,233 | A | | 1/1969 | Kanof |
| 3,543,760 | A | | 12/1970 | Bolduc |
| 3,596,657 | A | | 8/1971 | Eidus ......................... 128/156 |
| 3,799,162 | A | | 3/1974 | Romero-Sierra et al. |
| 3,800,792 | A | * | 4/1974 | McKnight et al. .............. 602/50 |
| 3,814,097 | A | | 6/1974 | Ganderton et al. |
| 3,817,253 | A | | 6/1974 | Gonser |
| 3,830,908 | A | | 8/1974 | Klippel et al. |
| 3,845,771 | A | | 11/1974 | Vise |
| 3,864,160 | A | | 2/1975 | Davidoff |
| 3,911,906 | A | | 10/1975 | Reinhold, Jr. |
| 3,914,488 | A | * | 10/1975 | Gorrafa ........................ 428/397 |
| 3,934,066 | A | | 1/1976 | Murch |
| 3,964,477 | A | | 6/1976 | Ellis et al. |
| 4,027,393 | A | | 6/1977 | Ellis et al. |
| 4,034,750 | A | | 7/1977 | Seiderman |
| 4,035,500 | A | * | 7/1977 | Dafter, Jr. ...................... 427/261 |
| 4,042,737 | A | | 8/1977 | Forsgren et al. |
| 4,142,521 | A | * | 3/1979 | Konikoff ........................... 602/2 |
| 4,161,470 | A | | 7/1979 | Calundann |
| 4,181,127 | A | | 1/1980 | Linsky et al. |
| 4,213,463 | A | | 7/1980 | Osenkarski |
| 4,240,437 | A | | 12/1980 | Church |
| 4,291,125 | A | | 9/1981 | Greatbatch |
| 4,297,995 | A | | 11/1981 | Golub |
| 4,312,340 | A | | 1/1982 | Donadelli |
| 4,313,438 | A | | 2/1982 | Greatbatch |
| 4,333,449 | A | | 6/1982 | Muller et al. |
| 4,420,529 | A | * | 12/1983 | Westhead ...................... 442/187 |
| 4,456,001 | A | | 6/1984 | Pescatore |
| 4,476,590 | A | | 10/1984 | Scales et al. |
| 4,486,488 | A | | 12/1984 | Pietsch et al. |
| 4,509,535 | A | | 4/1985 | Bryan |
| 4,510,939 | A | | 4/1985 | Brenman et al. |
| 4,525,410 | A | * | 6/1985 | Hagiwara et al. ............. 428/198 |
| 4,528,265 | A | | 7/1985 | Becker |
| 4,529,623 | A | | 7/1985 | Maggs |
| 4,541,426 | A | * | 9/1985 | Webster ........................... 602/47 |
| 4,551,139 | A | | 11/1985 | Plaas et al. |
| 4,554,923 | A | | 11/1985 | Batters |
| 4,556,051 | A | | 12/1985 | Maurer |
| 4,563,184 | A | | 1/1986 | Korol |
| 4,588,400 | A | | 5/1986 | Ring et al. |
| 4,600,001 | A | | 7/1986 | Gilman |
| 4,606,338 | A | | 8/1986 | Greenway et al. |
| 4,615,705 | A | | 10/1986 | Scales et al. |
| 4,619,252 | A | * | 10/1986 | Ibbott .............................. 602/2 |
| 4,635,624 | A | | 1/1987 | Gilman |
| 4,646,730 | A | | 3/1987 | Schonfeld et al. |
| 4,654,323 | A | | 3/1987 | Beitner |
| 4,664,118 | A | | 5/1987 | Batters |
| 4,671,266 | A | | 6/1987 | Lengyel et al. |
| 4,728,323 | A | * | 3/1988 | Matson ........................ 604/304 |
| 4,747,845 | A | | 5/1988 | Korol |
| 4,757,804 | A | | 7/1988 | Griffith et al. |
| 4,767,401 | A | | 8/1988 | Seiderman |
| 4,781,705 | A | | 11/1988 | Shepherd et al. |
| 4,798,603 | A | | 1/1989 | Meyer et al. |
| 4,817,594 | A | * | 4/1989 | Juhasz ............................ 602/42 |
| 4,818,697 | A | | 4/1989 | Liboff et al. |
| 4,825,877 | A | | 5/1989 | Kempe |
| 4,847,049 | A | | 7/1989 | Yamamoto |
| 4,852,453 | A | * | 8/1989 | Morin ............................ 89/1.11 |
| 4,867,150 | A | | 9/1989 | Gilbert |
| 4,867,166 | A | | 9/1989 | Axelgaard et al. |
| 4,886,505 | A | | 12/1989 | Haynes et al. |
| 4,889,530 | A | | 12/1989 | Smith et al. |
| 4,909,244 | A | | 3/1990 | Quarfoot |
| 4,911,688 | A | | 3/1990 | Jones |
| 4,932,951 | A | | 6/1990 | Liboff et al. |
| 4,935,087 | A | | 6/1990 | Gilman |
| 4,937,323 | A | | 6/1990 | Silver et al. |
| 4,960,413 | A | | 10/1990 | Sagar et al. |
| 4,979,946 | A | | 12/1990 | Gilman |
| 4,982,742 | A | | 1/1991 | Claude |
| 4,984,570 | A | * | 1/1991 | Langen et al. .................. 602/44 |
| 4,990,144 | A | | 2/1991 | Blott |
| 4,997,425 | A | | 3/1991 | Shioya et al. |
| 5,018,515 | A | | 5/1991 | Gilman |
| 5,018,516 | A | | 5/1991 | Gilman |
| 5,019,096 | A | | 5/1991 | Fox, Jr. et al. |
| 5,038,797 | A | | 8/1991 | Batters |
| 5,042,466 | A | | 8/1991 | McKnight |
| 5,049,139 | A | | 9/1991 | Gilchrist |
| 5,056,510 | A | | 10/1991 | Gilman |
| 5,067,478 | A | | 11/1991 | Berlant |
| 5,130,342 | A | | 7/1992 | McAllister et al. |
| 5,133,199 | A | | 7/1992 | Parikh et al. |
| 5,147,338 | A | | 9/1992 | Lang et al. |
| 5,147,344 | A | | 9/1992 | Sachau et al. |
| 5,158,555 | A | | 10/1992 | Porzilli |
| 5,167,613 | A | | 12/1992 | Karami et al. |
| 5,180,585 | A | | 1/1993 | Jacobson et al. |
| 5,181,905 | A | | 1/1993 | Flam |
| 5,185,000 | A | | 2/1993 | Brandt et al. |
| 5,266,371 | A | | 11/1993 | Sugii et al. |
| 5,275,861 | A | | 1/1994 | Vaughn |
| 5,288,544 | A | * | 2/1994 | Mallen et al. .................. 442/198 |
| 5,292,589 | A | | 3/1994 | Shepherd et al. |
| 5,298,015 | A | | 3/1994 | Komatsuzaki et al. |
| 5,306,229 | A | | 4/1994 | Brandt et al. |
| 5,308,313 | A | | 5/1994 | Karami et al. |
| 5,320,908 | A | | 6/1994 | Sodervall et al. |
| 5,322,520 | A | | 6/1994 | Milder |
| 5,324,275 | A | | 6/1994 | Raad et al. |
| 5,326,567 | A | | 7/1994 | Capelli |
| 5,333,753 | A | | 8/1994 | Etheredge |
| 5,340,363 | A | | 8/1994 | Fabo |
| 5,360,440 | A | * | 11/1994 | Andersen ...................... 607/115 |
| 5,374,283 | A | | 12/1994 | Flick |
| 5,395,305 | A | * | 3/1995 | Koide et al. ..................... 602/48 |
| 5,395,398 | A | | 3/1995 | Rogozinski |
| 5,405,644 | A | | 4/1995 | Ohsumi et al. |
| 5,413,788 | A | | 5/1995 | Edwards et al. |
| 5,419,161 | A | | 5/1995 | Bodenschatz et al. |
| 5,429,590 | A | | 7/1995 | Saito et al. |
| 5,429,591 | A | | 7/1995 | Yamamoto et al. |
| 5,433,987 | A | * | 7/1995 | Peterson et al. .............. 428/137 |
| 5,454,886 | A | | 10/1995 | Burrell et al. |
| 5,465,735 | A | | 11/1995 | Patel |
| 5,470,576 | A | | 11/1995 | Patel |
| 5,470,585 | A | | 11/1995 | Gilchrist |
| 5,512,041 | A | | 4/1996 | Bogart |
| 5,520,664 | A | | 5/1996 | Bricault et al. |
| 5,543,151 | A | | 8/1996 | Shirai et al. |
| 5,569,207 | A | | 10/1996 | Gisselberg et al. |
| 5,571,079 | A | | 11/1996 | Bello et al. |
| 5,571,521 | A | | 11/1996 | Lasker |
| 5,584,877 | A | * | 12/1996 | Miyake et al. ............... 623/1.42 |
| 5,591,790 | A | | 1/1997 | Lock |
| 5,595,750 | A | | 1/1997 | Jacobson et al. |
| 5,607,683 | A | | 3/1997 | Capelli |
| 5,632,731 | A | | 5/1997 | Patel |
| 5,660,178 | A | * | 8/1997 | Kantner et al. ............... 600/391 |
| 5,662,913 | A | | 9/1997 | Capelli |
| 5,681,575 | A | | 10/1997 | Burrell et al. |
| 5,690,955 | A | * | 11/1997 | Griffiths et al. ............... 424/443 |
| 5,695,857 | A | | 12/1997 | Burrell et al. |
| 5,714,225 | A | | 2/1998 | Hansen et al. |
| 5,744,151 | A | | 4/1998 | Capelli |
| 5,753,251 | A | | 5/1998 | Burrell et al. |
| 5,770,255 | A | * | 6/1998 | Burrell et al. .................. 427/2.1 |
| 5,772,620 | A | | 6/1998 | Szlema et al. |
| 5,779,659 | A | | 7/1998 | Allen |
| 5,782,785 | A | | 7/1998 | Herzberg |
| 5,782,788 | A | * | 7/1998 | Widemire ...................... 602/48 |
| 5,789,326 | A | | 8/1998 | Hansen et al. |
| 5,814,094 | A | * | 9/1998 | Becker et al. ................... 607/50 |
| 5,824,267 | A | | 10/1998 | Kawasumi et al. |
| 5,836,970 | A | | 11/1998 | Pandit |
| 5,844,013 | A | | 12/1998 | Kenndoff et al. |
| 5,882,677 | A | | 3/1999 | Kupperblatt |
| 5,895,419 | A | * | 4/1999 | Tweden et al. ............... 623/2.36 |
| 5,921,948 | A | | 7/1999 | Kawaguchi et al. |

| | | | |
|---|---|---|---|
| 5,974,344 A | 10/1999 | Shoemaker, II | 607/149 |
| 5,983,136 A | 11/1999 | Kamen | |
| 5,985,301 A | 11/1999 | Nakamura et al. | |
| 5,985,308 A | 11/1999 | Burrell et al. | |
| 5,998,692 A | 12/1999 | Gilding | |
| 6,004,667 A * | 12/1999 | Sakurada et al. | 428/323 |
| 6,014,585 A * | 1/2000 | Stoddard | 607/2 |
| 6,063,980 A * | 5/2000 | Peterson et al. | 602/49 |
| 6,074,965 A | 6/2000 | Bodenschatz et al. | |
| 6,087,549 A | 7/2000 | Flick | |
| 6,093,414 A | 7/2000 | Capelli | |
| 6,099,489 A | 8/2000 | Herzberg et al. | |
| 6,120,470 A | 9/2000 | Bodenschatz et al. | |
| 6,129,694 A | 10/2000 | Bodenschatz | |
| 6,139,856 A | 10/2000 | Kaminska et al. | |
| 6,149,616 A | 11/2000 | Szlema et al. | |
| 6,160,196 A | 12/2000 | Knieler et al. | |
| 6,171,648 B1 | 1/2001 | Himmelsbach et al. | |
| 6,180,544 B1 | 1/2001 | Jauchen et al. | |
| 6,190,407 B1 | 2/2001 | Ogle et al. | |
| 6,191,337 B1 | 2/2001 | Himmelsbach | |
| 6,210,704 B1 | 4/2001 | Sasaki et al. | |
| 6,224,898 B1 | 5/2001 | Balogh et al. | |
| 6,224,983 B1 | 5/2001 | Sodervall et al. | |
| 6,245,959 B1 | 6/2001 | Ohira et al. | |
| 6,248,932 B1 | 6/2001 | Himmelsbach | |
| 6,267,743 B1 | 7/2001 | Bodenschatz et al. | |
| 6,267,782 B1 | 7/2001 | Ogle et al. | |
| 6,274,205 B1 | 8/2001 | Himmelsbach et al. | |
| 6,284,328 B1 | 9/2001 | Leydecker et al. | |
| 6,322,588 B1 | 11/2001 | Ogle et al. | |
| 6,333,093 B1 * | 12/2001 | Burrell et al. | 428/194 |
| 6,348,212 B2 | 2/2002 | Hymes et al. | |
| 6,350,247 B2 | 2/2002 | Bodenschatz et al. | |
| 6,355,858 B1 | 3/2002 | Gibbins | |
| 6,383,630 B1 | 5/2002 | Jauchen et al. | |
| 6,428,800 B2 | 8/2002 | Greenspan et al. | |
| 6,436,420 B1 | 8/2002 | Antelman | |
| 6,447,470 B2 | 9/2002 | Bodenschatz et al. | |
| 6,459,013 B1 | 10/2002 | Himmelsbach | |
| 6,495,230 B1 | 12/2002 | do Canto | |
| 6,506,957 B1 | 1/2003 | Himmelsbach et al. | |
| 6,524,699 B1 | 2/2003 | Himmelsbach et al. | |
| 6,551,704 B2 | 4/2003 | Himmelsbach et al. | |
| 6,555,730 B1 | 4/2003 | Albrod et al. | |
| 6,569,111 B2 | 5/2003 | Herzberg | |
| 6,579,539 B2 | 6/2003 | Lawson et al. | |
| 6,582,713 B2 | 6/2003 | Newell et al. | |
| 6,592,888 B1 | 7/2003 | Jensen et al. | |
| 6,599,525 B2 | 7/2003 | Scamilla Aledo et al. | |
| 6,605,751 B1 | 8/2003 | Gibbins et al. | |
| 6,617,485 B2 | 9/2003 | Herzberg | |
| 6,656,491 B1 | 12/2003 | Brosch et al. | |
| 6,695,824 B2 | 2/2004 | Howard et al. | |
| 6,706,279 B1 | 3/2004 | Hazzi | |
| 6,713,659 B2 | 3/2004 | Bodenschatz et al. | |
| 6,716,895 B1 | 4/2004 | Terry | |
| 6,730,053 B1 | 5/2004 | Bodenschatz et al. | |
| 6,822,132 B2 | 11/2004 | Ahrens et al. | |
| 6,852,366 B2 | 2/2005 | Zschaeck | |
| 6,861,570 B1 | 3/2005 | Flick | |
| 6,897,349 B2 | 5/2005 | Gibbins et al. | |
| 7,005,556 B1 * | 2/2006 | Becker et al. | 602/48 |
| 2001/0055608 A1 | 12/2001 | Hymes et al. | |
| 2002/0132545 A1 | 9/2002 | Lenz | |
| 2002/0150720 A1 | 10/2002 | Howard et al. | |
| 2002/0156411 A1 | 10/2002 | Ahrens et al. | |
| 2002/0172709 A1 | 11/2002 | Nielsen et al. | |
| 2002/0197257 A1 | 12/2002 | Meyer-Ingold et al. | |
| 2003/0091736 A1 | 5/2003 | Zschaeck | |
| 2003/0104039 A1 | 6/2003 | Berthold et al. | |
| 2003/0170314 A1 | 9/2003 | Burrell et al. | |
| 2003/0176827 A1 | 9/2003 | Chandra et al. | |
| 2003/0185901 A1 | 10/2003 | Burrell et al. | |
| 2003/0208150 A1 | 11/2003 | Bruder et al. | |
| 2004/0002675 A1 | 1/2004 | Nierle et al. | |
| 2004/0009202 A1 | 1/2004 | Woller | |
| 2004/0010215 A1 | 1/2004 | Gibbins et al. | |
| 2004/0049145 A1 | 3/2004 | Flick | |
| 2004/0058013 A1 | 3/2004 | Taylor et al. | |
| 2004/0086549 A1 | 5/2004 | Nielsen | |
| 2004/0091521 A1 | 5/2004 | Radloff et al. | |
| 2005/0187580 A1 * | 8/2005 | Skiba | 607/2 |
| 2005/0244484 A1 | 11/2005 | Flick | |
| 2008/0033506 A1 | 2/2008 | Flick | |
| 2008/0064997 A1 | 3/2008 | Flick | |
| 2008/0114279 A1 | 5/2008 | Becker et al. | |
| 2008/0119773 A1 | 5/2008 | Flick | |
| 2008/0125687 A1 | 5/2008 | Flick et al. | |

FOREIGN PATENT DOCUMENTS

| | | |
|---|---|---|
| EP | 0 128 338 | 12/1984 |
| EP | 0 254 413 | 1/1988 |
| EP | 0 291 587 | 11/1988 |
| EP | 0 344 090 | 11/1989 |
| EP | 0344090 | 11/1989 |
| EP | 0 354 315 | 2/1990 |
| EP | 0 367 320 | 5/1990 |
| EP | 0 392 640 | 10/1990 |
| EP | 1 159 972 | 5/2001 |
| GB | 363255 | 6/1930 |
| GB | 863875 | 3/1961 |
| GB | 2 092 006 | 8/1982 |
| GB | 2127389 | 4/1984 |
| GB | 2 134 791 | 8/1984 |
| GB | 2188135 | 9/1987 |
| JP | S56-166041 U | 12/1981 |
| JP | 58-209356 | 12/1983 |
| JP | 62-275456 | 11/1987 |
| JP | 3-146057 | 6/1991 |
| JP | 3-253575 | * 11/1991 |
| WO | WO 90/08470 | 8/1990 |
| WO | WO 91/11206 | 8/1991 |
| WO | WO 92/13491 | 8/1992 |
| WO | WO 93/23092 | 11/1993 |
| WO | WO 96/13282 | 5/1996 |
| WO | WO 98/06509 | 2/1998 |
| WO | WO 99/15101 | 4/1999 |
| WO | WO 00/25726 | 5/2000 |
| WO | WO 00/73552 | 12/2000 |
| WO | WO 01/60599 | 8/2001 |
| WO | WO 02/099181 | 12/2002 |
| WO | WO 03/022317 | 3/2003 |
| WO | WO 03/057307 | 7/2003 |
| WO | 03 527200 | 9/2003 |
| WO | WO 2004/002384 | 1/2004 |
| WO | WO 2004/018020 | 3/2004 |
| WO | WO 2004/037186 | 5/2004 |
| WO | WO 2007/046806 | 4/2007 |

OTHER PUBLICATIONS

Online encyclopedia article "Magnetic field" accessed May 27, 2009. http://en.wikipedia.org/wiki/Magnetic_field.*

Online encyclopedia article "Resistivity" accessed Feb. 25, 2010. http://en.wikipedia.org/wiki/Electrical_resistivity.*

Deitch, E.A. et al, "Silver-Impregnated Nylon Cloth Dressing", Burns, vol. 13, Issue 5, p. 423, Oct. 1987.

MacKeen, P.C. et al., "Silver-Coated Nylon Fiber as an Antibacterial Agent", Antimicrobial Agents and Chemotherapy, American Society for Microbiology, vol. 31, No. 1, pp. 93-99, Jan. 1987.

Marino, A.A. et al., "Electric Silver Antiseptics", IEEE Transactions on Biomedical Engineering, vol. BME-32, No. 5, pp. 336-337, May 1985.

Marino, A.A. et al., "Electrical Augmentation of the Anitmicrobial Activity of Silver-Nylon Fabrics", Journal of Biological Physics, vol. 12, 1984.

McManus, A.T. "The Burn Wound: Effect of Silver Mylon Dressing and DC", Pathoshysiology, vol. 1, Supplement 1, p. 121, Nov. 1994.

Riggle, P.J. et al., "Role of a *Candida albicans* P1-Type ATPase in Resistance to Copper and Silver Ion Toxicity", Journal of Bacteriology, American Society for Microbiology, vol. 182, No. 17, pp. 4899-4905, Sep. 2000.

Schierholz, J.M. et al., "Efficacy of Silver-coated Medical Devices", Journal of Hospital Infection, vol. 40 pp. 257-262, 1998.

Amended Complaint—*Noble Fiber Technologies, LLC* v. *Argentum Medical, LLC et al.*, Civil Action Case No. 3:05-cv-01855-ARC filed Oct. 21, 2005.
Complaint—*Noble Fiber Technologies, LLC* v. *Argentum Medical, LLC*, Civil Action No. 3:05-CV-01855-ARC, filed Sep. 13, 2005.
Partial European Search Report for EP 98 94 9403 dated Jul. 2, 2004.
Khanna, A., Sivaraman, R., and Vohora S.B. *Analgesic Activity of Silver Preparations Used in Indian Systems of Medicine.* Indian Journal of Pharmacology, 1997, 29:393-398.
Becker R.O. and Spadaro J.A., *Treatment of Orthopaedic Infections with Electrically Generated Silver Ions*, Journ. of Bone and Joint Surgery, Oct. 1978, vol. 60-A, No. 7, pp. 871-881.
Berger T.J., Spadaro J.A., Bierman, R., Chapin S.E., Becker R.O., *Antifungal Properties of Electrically Generated Metallic Ions.*, Atimicrobial-Agents and Chemotherapy, Nov. 1976, vol. 10, No. 5, pp. 856-860.
Foulds, I.S. and Barker A.T. *Human skin battery potentials and their possible role in wound healing*, British Jorn. of Dermatology, Mar. 1983, 109 pp. 515-522.
Friedenberg Z.B. *Bioelectric Potentials in Bone.* Journ. of Bone and Joint Surgery, Jul. 1966, vol. 48-A, No. 5, pp. 915-923.
Illingworth, C.M and Barker A.T. *Measurement of Electrical Currents Emerging During the Regeneration of Amputated Finger Tips in Children*, Clin. Phys. Physiological Measurements, 1980, vol. 1, No. 1, pp. 87-89.
Jaffe, L.F. and Vanable J.W., Jr. *Electric Fields and Wound Healing*, Clinics in Dermatology, Jul.-Sep. 1984, vol. 2, No. 3, pp. 34-44.
McCaffery M., Pasero C., Pain: *Clinical Manual*, Second Edition, Mosby, pp. 62-65.
Ohnhaus E.E. and Adler R. *Methodological Problems in the Measurement of Pain: A Comparison Between the Verbal Rating Scale and the Visual Analouge Scale*, Pain, 1975, Elsevier/North-Holland, Amsterdam, pp. 379-384.
Pain Assessment and Management: An Organizational Approach, Joint Commission, Chapter Three: Assessment of Persons with Pain, pp. 13-25.
Smee L., *The Effectiveness of Silver Nylon Cloth and Silver Sulfadiazine Cream as Antiseptics*, Piedmont College Senior Thesis, Apr. 1996, USA.
Sriwatanakul K., Kelvie W., Lasagna L., Calimlim, J.F., Weis O.F., Mehta G. *Studies with Different Types of Visual Analog Scales for Measurement of Pain*, Dept. of Pharmacol. Ther., Aug. 1983, pp. 234-239.
Spadaro J.A., Berger T.J., Barranco S.D., Chapin S.E., Becker R.O. *Antibacterial Effects of Silver Electrodes with Weak Direct Current*, Atimicrobial-Agents and Chemotherapy., Nov. 1974, vol. 6, No. 5, pp. 637-642.
Vanable J.W., Jr. *Integumentary Potentials and Wound Healing*, Elec. Fields in Vertebrate Repair, 1989, pp. 171-224.
Westaim Biomedical Commercial Literature, bearing 1988 Copyright notice and product label bearing Acticoat. RTM.
U.S. Appl. No. 09/613,961, filed Jul. 11, 2000, Flick.
U.S. Appl. No. 11/220,566, filed Sep. 6, 2005, Becker et al.
U.S. Appl. No. 11/255,492, filed Oct. 21, 2005, Flick et al.
Becker et al., "Clinical Exp. With Low Intensity Direct Current Stimulation of Bone Growth," *Clin. Orthop. & Rel. Res.*, (1977) vol. 124, pp. 75-83.
Becker et al., "Electrochemical Mechanisms and the Control of Biological Growth Processes," *Modern Aspects of Electrochemistry*, (1971) No. 10, pp. 289-338.
Becker et al., "Experience with Low-Current Silver Electrode Treatment of Nonunion," *Electrical Prop. Bone & Cartilage* (ed. C.T. Brighton, et al.), (1979).
Berger et al., "Electrically Generated Silver Ions: Quantitative Effects on Bacterial & Mammalian Cells," *Antimicrob. Agents & Chemother*, (1976) vol. 9, pp. 397-358.
Deitch et al., "Silver-Nylon: A New Antimicrobial Agent," *Antimicrobial Agents and Chemotherapy*, (Mar. 1983) pp. 356-359.
Hill et al., "Inhibitory and Cidal Antimicrobial Actions of Electrically Generated Silver Ions," *J. Oral & Maxillofac. Surg.*, (1987) vol. 45, pp. 779-784.

Marino et al., "Electrochemical Properties of Silver-Nylon Fabrics," *Electrochemical Science and Technology*, (1985) vol. 132, No. 1, pp. 68-72.
Spadaro et al., "Experience with Anodic Silver in the Treatment of Osteomyelitis," $25^{th}$ Ann. ORS Mtg., (Feb. 20-22, 1979).
Spadaro et al., "Some Specific Cellular Effects of Electrically Injected Silver & Gold Ions," *Bioelectrochem. & Bioenergetics*, (1976) vol. 3, pp. 49-57.
Urist et al., "Bone Morphogenesis in Implants of Insoluble Bone Gelatin," *Proc. Nat. Acad. Sci USA*, (1973) vol. 70, No. 12, Part I, pp. 3511-3515.
U.S. Appl. No. 08/707,779, Becker et al.
Complaint—*Argentum Medical, LLC* v. *Noble Biomaterials and Derma Sciences, Inc.*, Civil Action Case No. 1:07-cv-06769 filed Dec. 3, 2007.
Burrell, et al, "Efficacy of Silver-Coated Dressings as Bacterial Barriers in a Rodent Burn Sepsis Model", *Wounds*, 11(4): 64-71 (1999).
Butts, et al, Silver: Economics, Metallurgy, and Use, Table of Contents and Chapter 17, pp. 227-234, Van Norstrand Company, Inc., Princeton, New Jersey (1967).
Chu, et al, "Newly Made Antibacterial Braided Nylon Sutures—I. In Vitro Qualitative and In Vivo Preliminary Biocompatibility Study", *J. of Biomedical Materials Research*, 21: 1281-1300 (1987).
Federal Food and Drug Administration Form 510(k) Summary for Silverlon.
Federal Food and Drug Administration Form 510(k) Summary for Westaim Technologies, Inc.'s Anticoat™ Silver Coated Dressings.
Thurman, et al, "The Molecular Mechanisms of Copper and Silver Ion Disinfection of Bacteria and Viruses"; *CRC Critical Reviews in Environmental Controls*, 18(4) (1989).
Tredget, et al, "A Matched-Pair, Randomized Study Evaluating the Efficacy and Safety of Anticoat Silver-Coated Dressing for the Treatment of Burn Wounds", *J. Burn Care Rehab*, 19: 531-537 (1998).
Tsai, et al, "In Vitro Quantitative Study of Newly Made Antibacterial Braided Nylon Structures", *Surgery, Gynecology, & Obstetrics*, 165: 207-211 (1987).
Wright, et al, "Wound Management in an Era of Increasing Bacterial Antibiotic Resistance: A Role for Topical Silver Treatment", *AJIC Am J Infect Control*, 26: 572-777 (1998).
Wright, et al., "Efficacy of Topical Silver Against Fungal Burn Wound Pathogens", *AJIC Am J Infection Control*, 27: 344-350 (1999).
Yin, et al, "Comparative Evaluation of the Antimicrobial Activity of ACTICOAT Antimicrobial Barrier Dressing", *J. Burn Care Rehab*, 20: 195-200 (1999).
Barker, et al., "The glabrous epidermis of cavies contains a powerful battery", *Am. J. Physiol.*, 242(3):R358-66 (1982).
Borgens, "What is the role of naturally produced electric current in vertebrate regeneration and healing", *Int. Rev. Cytol.*, 76:245-98 (1982).
Eaglstein, "Current wound management: a symposium", *Clin. Dermatol.*, 2(3):134-42 (1984).
Eckersley and Dudley, "Wounds and wound healing", *Br. Med. Bull.*, 44(2):423-36 (1988).
Winter, et al., Movement of epidermal cells over the wound surface in: Montagne W. & Billingham R.E Advances in Biology of the skin. vol. 5. pp. 113-127. Wound Healing. New York. The MacMillan Company (1964).
Deitch, et al. "Silver nylon cloth: In vitro and in vivo evaluation of antimicrobial activity", *J. Trauma*, 27(3): 301-304 (1987).
Becker, "Expert Opinion", date-stamped Nov. 13, 1986.
Bertuleit, "Elektrische leitfähigkeit auf polyamiden durch versilberung", *International Textile Reports*, Dec. 1990.
Bertuleit, "Elektrische leitfähigkeit auf polyamiden durch versilberung", *Techtex Forum*, Nov. 1990: 20-22.
Bertuleit, "Neue möglichkeiten für smart textiles mit leitfähigen silberfäden", http://www.statex.biz/ger/index.php?varx=smart, pp. 1-4 (accessed Jan. 22, 2009).
Bertuleit, "Silver coated polyamide: a conductive fabric", *J. Coated Fabrics*, (20): 211-215 (1991).
Chu, et al. "Multiple graft harvestings from deep partial-thickness scald wounds healed under the influence of weak direct current", *J. Trauma*, 30(8):1044-9; discussion 1049-50 (1990).

Chu, et al. "The use of transplantable dermis from incompatible host in composite skin grafts: paper 54", *Proceedings ABA 33rd Annual Meeting* (Boston, MA); p. S73 (2001).

Chu, et al. "Therapeutic effects of silver nylon dressings with weak direct current on pseudomonas aeruginosa-infected burn wounds", *J. Trauma*, 28(10):1488-92 (1988).

Chu, et al., "Direct current reduces wound edema after full-thickness burn injury in rats", *J. Trauma*, 40(5):738-42 (1996).

Chu, et al., "Enhanced survival of autoepidermal-allodermal composite grafts in allosensitized animals by use of silver-nylon dressings and direct current", *J. Trauma*, 39(2):273-7; discussion 277-8 (1995).

Chu, et al., Weak direct current accelerates split-thickness graft healing on tangentially excised second-degree burns, *J. Burn Care Rehabil.*, 12(4):285-93 (1991).

Norm Din 54345 Teil 1, Prüfung von textilien elektrostatisches verhalten bestimmung eletrischer widerstandsgrössen (1992).

Andron, et al., "Silver nylon (SN) dressings reduce leakage of Evans blue dye-albumin (EBA) into burn wounds", Abstract #1398; p. A242; Presented at Experimental Biology 1993 (Federation of American Societies of for Experimental Biology (FASEB)), New Orleans, LA, Mar. 28-Apr. 1, 1993.

Chu, et al., "Therapeutic effects of silver-nylon dressings with weak direct current on Psuedomonas Auerginosa infected burn wounds", Abstract #64, vol. 17, 1 page, *American Burn Association, Seventeenth Annual Meeting*, Mar. 27-30, 1985.

Chu, et al. "Reduction of dermal ischemia (zone of stasis) by post scald application of weak direct current (DC)", *Proceedings of the American Burn Association*, vol. 25, Abstract #65, 1 page (1993). Presented at the 25th Annual Meeting of the American Burn Association, Cincinnati, OH, Mar. 24-27, 1993.

Chu, et al. "Silver-nylon (SN) and direct current (DC) reduce wound accumulation of Evans blue (EB) following full thickness thermal injury", *Wound Repair and Regeneration*, 3(1): abstract #90, 1 page, (1995). Presented at the 5th Annual Scientific Meeting of the Wound Healing Society, Minneapolis, MN, Apr. 27-30, 1995.

Chu, et al., "Reduced contraction and hair loss after healing of guinea pig scalds treated with direct current", *Wound Repair and Regeneration*, 2(1): abstract, 1 page, (1994). Presented at the 4th Annual Wound Healing Society Meeting, San Francisco, CA, May 18-20, 1994.

Chu, et al., "Accelerating split thickness graft healing on tangentially excised deep second degree burn wounds by weak direct current application", *Proceedings of the American Burn Association*, vol. 21, Abstract #62, 1 page, (1989). Twenty-First Annual Meeting, New Orleans, LA, Mar. 29-Apr. 1, 1989.

Chu, et al., "Direct current improves healing of composite autoepidermal/ allodermal grafts", *Proceedings of the American Burn Association*, vol. 26, Abstract #125, 1 page (1994). Presented at the 26th annual meeting of the American Burn Association, Orlando, FL, Apr. 20-23, 1994.

Chu, et al., "Effect of delay of direct current application on healing of partial thickness burns in Guinea pigs", *Wound Repair and Regeneration*, 4(1): abstract A147, 2 pages, (1996). Presented at 2nd Joint Meeting of the Wound Healing Society and The European Tissue Repair Society, Boston, MA, May 15-19, 1996.

Chu, et al., "Healing of second mesh auto-epidermal/allodermal composite graft without immunosuppressive treatment", Proceedings of the American Burn Association, abstract 4, p. 44, (1996). Presented at the 28th Annual Meeting of the American Burn Association, Nashville, TN, Mar. 14-17, 1996.

Chu, et al., "Improved healing and expansion with animal growth of deep partial thickness scalds treated with weak direct current silver-nylon dressings", *Proceedings of the American Burn Association*. vol. 23, abstract #172, (1991). Presented at the 23rd Annual Meeting of the American Burn Association, Baltimore, MD, Apr. 3-6, 1991.

Chu, et al., "Iontophoretic treatment of *P. mirabilis* burn wound sepsis using silver nylon dressings", *Abstracts of the 90th Annual Meeting of the American Society for Microbiology*, abstract A138, 1 page, (1990). Presented at the 1990 ASM Annual Meeting, Anaheim, CA, May 13-17, 1990.

Chu, et al., "Multiple graft harvesting from donor wounds healed under the influence of weak direct current", *Proceedings of the American Burn Association*, vol. 21, abstract #162, 1 page, (1989). Twenty-First Annual Meeting, New Orleans, LA, Mar. 29-Apr. 1, 1989.

Chu, et al., "Optimized mesh expansion of composite skin grafts in rats treated with direct current", *J. Trauma* 43(5):804-811 (1997).

Chu, et al., "Salvage of experimental full thickness scalds with cooling and weak anodal direct current", *Proceedings of the American Burn Association*, vol. 19, abstract #175, 1 page (1987). Nineteenth Annual Meeting, Washington, DC, Apr. 29-May 2, 1987.

Declaration of Andrew A. Marino, executed Jan. 24, 2011.

LexisNexis Case Summary—*Argentum Medical, LLC*, Plaintiff, v. *Noble Biomaterials, and Derma Sciences, Inc.*, Defendants. *Noble Biomaterials*, Counter-Claim Plaintiff, v. *Argentum Medical, LLC, Thomas Miller and Gregg Silver*, Counter-Claim Defendants.—No. 3:08-CV-1305, 2010 U.S. Dist. Lexis 66037, 7 pages, (accessed Jul. 23, 2010).

Detailed Request for *Ex Parte* Reexamination of U.S. Patent No. 7,230,153, filed Jan. 24, 2011, including Exhibits 2, 3, 6, and 18-21, letter from Scott E. Kambolz, and the Request for *Ex Parte* Reexamination Transmittal Form from Choice Therapeutics, Inc., dated Jan. 24, 2011.

Matylevich, et al., "Direct current (DC) reduces leakage and accumulation of macromolecules in full thickness burn injuries", *Proceedings of the American Burn Association*, vol. 26, abstract #144, 1 page (1994). Presented at the 26th annual meeting of the American Burn Association, Orlando, FL, Apr. 23, 1994.

Matylevich, et al., "Differential effect of direct current on extravasation of macromolecules following burn injury in rats", *Proceedings of the American Burn Association Twenty-Ninth Annual Meeting*, Abstract #33, p. S86 (1997). Twenty-ninth Annual Meeting of the American Burn Association, New York, NY, Mar. 19-22, 1997.

Matylevich, et al., "Direct current (DC) reduces albumin extravasation after partial thickness burn injury in rats", *Wound Repair and Regeneration*, 3(1): abstract 126, p. 97, (1995). Presented at the 5th Annual Scientific Meeting of the Wound Healing Society, Minneapolis, MN, Apr. 27-30, 1995.

Matylevich, et al., "Direct current (DC) reduces plasma extravasation after partial thickness burn injury in rats", *Proceedings of the American Burn Association*, abstract 170, 1 page (1995). Presented at the 27th Annual Meeting of the American Burn Association, Albuquerque, NM, Apr. 19-22, 1995.

Matylevich, et al., "Direct current reduces plasma protein extravasation after partial-thickness burn injury in rats", *J. Trauma*, 41(3):424-429 (1996).

Matylevich, et al., "Direct electric current inhibits apoptotic activity in partial thickness burn wounds in rats", *Wound Generation and Repair*, abstract 164, 2 pages (1996). Presented at 1996 2nd Joint Meeting of the Wound Healing Society and the European Tissue Repair Society, Boston, MA, May 17, 1996.

McManus, et al. "Mechanisms of in vitro sensitivity to sulfadiazine silver", *Arch. Surg.*, 118(2):161-166 (1983).

McManus, et al., "Studies on the mechanisms of in vitro resistance to silver sulfadiazine", *Proceedings of the Twelfth Annual Meeting of the American Burn Association*, abstract #34, p. 68 (1980). San Antonio, TX, Mar. 27-29, 1980.

McManus, et al., "Studies on the mechanisms of in vitro resistance to silver sulfadiazine", *Abstraction of the Annual Meeting of the American Society of Microbiology*, abstract A35, 1 page (1979). 79th Annual Meeting, Los Angeles, CA, May 4-8, 1979.

McManus, et al., "Assessment of in vitro minimal inhibitory concentrations of silver and ceriam ions on selected Gram-negative burn ward isolates", *Proceedings of the Tenth Annual Meeting of the American Burn Association*, abstract #10, p. 50, (1978). Birmingham, AL, Mar. 30-Apr. 1, 1978.

McManus & Chu, "Effective topical chemotherapy with silver-nylon (SN) dressings after excision of pseudomonas infected burn wounds", *Proceedings of the American Burn Association*, abstract #98, 1 page (1993). Presented at the 25th Annual Meeting of the American Burn Association, Cincinnati, OH, Mar. 24-27, 1993.

Wikipedia, "Magnetic Field," URL: http://en.wikipedia.org/wiki/Magnetic_field, accessed Jun. 28, 2010.

Detailed order granting request for *ex parte* reexamination of U.S. Patent No. 7,230,153 to Flick. The order was mailed Apr. 1, 2010.

Detailed Request for *Ex Parte* Reexamination of U.S. Patent No. 7,230,153 to Flick. The Request for Reexam was filed on Feb. 16, 2010.

Barillo, et al. "Effect of silver-nylon dressings and weak direct current on skin microcirculation", Shock, 3:42 (suppl) (1995).

Chu, et al., Accelerated healing with a mesh autograft / allodermal composite skin graft treated with silver nylon dressings with and without direct current in rats\, J Trauma, 49 (1): 115-125 (2000).

Chu, et al., "Direct current reduces accumulation of Evans Blue albumin in full thickness burns", J Trauma., 47 (2): 294-299 (1999).

Fox, "Silver sulfadiazene—a new topical therapy for Pseudomonas in burns. Therapy of Pseudomonas infections in burns", Arch Surg., 96 (2):184-188 (1968).

Goetz, et al., "The oligodynamic effect of silver", Silver in Industry, edited by L. Addicks, Reinhold Publishing, New York, Chapter 16 401-29 (1940).

Grabb, et al., "Cutting the skin graft", Plastic Surgery, Third edition , Little, Brown and Co., Boston MA, p. 24 (1979).

Krizek and Robson, "Evolution of quantitative bacteriology in wound management", Am. J. of Surgery, 130:579-584 (1975).

Moyer, et al., "Treatment of large human burns with 0.5% silver nitrate solution", Arch Surg., 90:812-867 (1965).

Office Action in U.S. Appl. No. 11/220,566, Office Action mailed Jul. 1, 2011.

Office Action in U.S. Appl. No. 11/745,237, Office Action mailed May 12, 2011.

Office Action in U.S. Appl. No. 11/927,065, Office Action mailed Nov. 1, 2010.

Office Action in U.S. Appl. No. 11/929,804, Office Action mailed Apr. 26, 2011.

Office Action in U.S. Appl. No. 11/930,541, Office Action mailed Mar. 22, 2011.

Office Action in U.S. Appl. No. 90/011,455, Office Action mailed Jun. 23, 2011.

Shirani, et al. Silver-nylon dressings promote painless healing:, Proc. Am. Burn Assoc, 25:66 (1993).

Stanford and Fox, "Clinical experience with silver sulfadiazene, a new topical agent for control of pseudomonas infection in burn patients" , J Trauma, 9 (5): 377-388 (1969).

US 5,872,068, 02/1999, Cartwright et al. (withdrawn)

\* cited by examiner

100μm

10 μm

114

40   41

1 μm

CONDUCTIVE WOUND DRESSINGS AND METHODS OF USE

CROSS REFERENCE TO RELATED APPLICATION

This application claims benefit to U.S. Provisional Application No. 60/374,769 filed Apr. 23, 2002. This application is also a continuation-in-part of U.S. patent application Ser. No. 09/531,245 filed Mar. 21, 2000, now U.S. Pat. No. 6,861,570 which is a continuation of pending prior International Application Serial No. PCT/US98/19689 filed on Sep. 22, 1998, which is a continuation-in-part of U.S. patent application Ser. No. 08/935,026 filed on Sep. 22, 1997, now U.S. Pat. No. 6,087,549, all of which are incorporated herein by reference in their entirety.

TECHNICAL FIELD OF THE INVENTION

The present invention relates to compositions and methods for the treatment of wounds. More particularly, it relates to moisture regulating wound dressings that maintain a moist wound healing environment, create a functional microbial barrier, reduce microbial bioburden of the wound, and aid in healing and pain reduction.

BACKGROUND OF THE INVENTION

The treatment of wounds has become a highly developed area of scientific and commercial investigation because increased rates of healing reduces healthcare costs and decreases the risk of complications due to secondary infections. It is currently believed that healing is related to the degree of injury, the immunological and nutritional status of the host, contamination of the wound, the maintenance of the moisture level, pH and oxygen tension of the wound surface, and the electrical parameters of the wound site in relation to the surrounding intact, uninjured tissue. In particular, regeneration in amphibians and fracture healing in mammals are associated with complex changes in the local direct current (DC) electric field. It is believed that the electric field gradually returns to normal pre-injury levels as the injury heals. Conversely, failure of the normal healing process, for example as in fracture non-unions, is associated with the absence of appropriate electrical signals at the site of the injury.

There have been numerous studies conducted on wound healing in amphibians because their rate of healing is significantly greater than that of mammals. Wound healing in mammalian skin occurs over days or even weeks, with epithelial cell migration rates ranging from 7 (dry wound) to 20 (wet wound) micrometers/hour. Amphibian skin wounds heal within hours, with epithelial cell migration rates ranging from 60 to more than 600 micrometers/hr. The expedited rates of healing in amphibian skin may be partially explained by the aqueous environment that bathes the outer surface of the epithelium. Amphibian wounds in an aqueous environment are provided with the appropriate ions to re-establish the electrical potential on the surface of the wound as well as provided with an environment favorable to cell migration and reproduction.

It is generally recognized that dry wounds in mammals heal more slowly than wounds that are kept moist by occlusive dressings. Keeping the epidermis surrounding a wound and the wound itself moist stimulates the wound to close. Wound dressings have been designed to retain moisture from the exudates produced by the wound and function by preventing evaporation of fluid. Wounds that are dry and lack production of exudate must depend upon the moisture within a self contained wound dressing. If the wound dressing dries out, the needed moisture level for optimum wound healing will not be maintained and the dressing will stick to the wound surface and cause disruption of cellular processes. The lack of moisture often results in the formation of an eschar or scab, and a general slowing of the wound healing process.

Wounds that produce an extensive amount of moisture are thought to create another problem called skin maceration. Skin maceration is a softening of the skin or wearing away of the skin as a result of continual exposure to bodily fluids or moisture. It is known to cause a breakdown of the cornified epithelium, thereby reducing the physical microbial barrier function as well as the moisture regulation function of the epidermis. With a reduction of the microbial barrier function, the wound surface has a significantly greater risk of contamination by pathogenic microbes from the surrounding environment. Therefore, it is common practice to design wound dressings to reduce or prevent skin maceration by wicking away wound fluids and storing the fluids in absorbent layers.

A common practice in the treatment of wounds is the application of impermeable backing sheets to a wound dressing. The backing sheet functions as a moisture retention layer as well as a physical barrier to prevent microbial penetration. The backing sheet typically consists of a material with specified moisture vapor transmission rates (MVTR) and provides control of the rate of evaporation of moisture from the absorbent layer. Therefore, the backing sheet is generally impervious to liquid.

There are a variety of venting systems that can be contained within the dressing structure for the purpose of directing wound exudates via specific pathways to provide a controlled leakage of fluids from the wound surface to a contained absorbent layer. For example, in certain perforated films, the perforations are sufficient to permit wound exudates to diffuse through the film at a rate that precludes pooling on the wound surface, which is a common cause of maceration. These dressings must be removed when they become saturated with exudates.

While there are numerous dressings designed to retain the moisture content of wounds, there are still many areas of inefficiency in current treatment methods. For example, these dressings are only effective for moist wounds and do not provide any significant benefit for dry wounds. Wounds vary significantly in the amount of exudates or moisture produced throughout the healing cycle. In order to maintain an effective level of moisture it is necessary to continually change the dressings as the absorbent component reaches maximum capacity. Conversely, it is necessary to remove the dressings and add fluid to dry wounds, then replace the dressings. In either situation, removal of the dressing can cause disruption of the cellular process of the wound and increase the risk of contamination by microbes. Furthermore, it is necessary to change the types of dressings throughout the healing process of the wound as the moisture content changes.

Besides the effect of moisture on wound healing, microbial growth at the site of injury has a great effect on healing. In normal skin, a microbial barrier is created by the cornified epithelium. Wounds cause destruction of the cornified epithelium as well as deeper layers thereto, and the loss of the natural anti-microbial barrier.

The presence of microbial species at the wound site creates a bioburden that can retard the healing process. As the bioburden of the wound decreases to bacterial counts less than $10^3$ CFU/ml, wound healing is enhanced. Treatment of wounds typically involves preventing contamination by pathogenic microbes from the external environment as well as reducing the microbial bioburden of the wound.

While there are scores of antibacterial and antifungal agents that can be used to treat wounds, the anti-microbial and antifungal properties of silver have been of particular interest. However, the effectiveness of silver as an anti microbial agent is at least partly determined by the delivery system. Most silver compounds that dissociate readily and produce large numbers of free silver ions are highly toxic to mammalian tissues. Less-toxic compounds, including silver sulfadiazine cream, widely used in the treatment of burns, do not dissociate readily and therefore do not release large numbers of silver ions. Therefore, these compounds must be re-applied frequently to maintain their clinical efficacy.

Silver has been used in the construction of wound dressings to actively or passively release metallic silver particles or silver ions into the wound. Active release of silver ions require the presence of an electrical potential that actively drives silver ions from a source into the wound dressing or wound itself. This has been accomplished with a battery or other power source known to those skilled in the art. Passive release of silver ions is dependent upon the solubility of silver in aqueous solutions. The passive release of silver ions has been called the oligodynamic release process and includes the passive dissolution of silver into a solution.

The anti-microbial efficiency of metallic silver or silver ions is dependent upon the microbe coming into direct contact with the surface of the metallic silver or coming into contact with a released silver ion. Therefore, the total surface area of metallic silver and the number of silver ions released is directly related to the level of anti-microbial activity. Various methods have been used to create mechanisms for metallic ion transfer.

For example, the vacuum vapor deposition technique has been utilized in the construction of wound dressings to plate metallic silver and silver salts onto a variety of substrates. The vacuum vapor deposition technique has been modified so as to create "atomic disorder" of the plated silver that has been reported to enhance the anti-microbial effect by allowing the release of nanocrystalline particles of metallic silver. However, the technique provides a flat plating pattern and does not uniformly coat the entire three-dimensional surface of fibers.

Another mechanism used for passive release of silver ions and particles from a wound dressing includes imbedding or placing silver particles of varying sizes in a variety of substrates. Finely divided metallic silver in collagen has been incorporated into surgical dressings of reconstituted collagen foam laminated to a thick continuous layer of inert polymer. This does not allow for direct contact of the maximum number of ions with the wound.

When connected to a voltage source, a metal anode and a return electrode have been used as a means to deliver silver ions iontophoretically to a wound or within a wound dressing. Electrically conductive silver-impregnated meshes, including silver-protein colloids, have been disclosed with current densities as low as 10 $\mu A/mm^2$. This requires an external power source and stationary equipment and is cumbersome for the patient.

Silver foils have been incorporated into wound dressings as a means of supplying silver ions as an anti-microbial agent, as well as acting as an electrode for dispensing medications. In addition, silver has been fabricated into devices that incorporate a means of applying a therapeutic voltage to the wound. Foils do not provide for circulation of air, and are limited in surface area.

Compounds that slowly release silver into the wound environment have been disclosed in substances such as water soluble glass, phosphorus pentoxide and silver oxide. The silver impregnated glass may be in the form of a powder, granules, or woven into a dressing. The water soluble glass releases silver secondary to the dissolution of the glass. Such compositions have a high volume resistance and very poor conductivity.

Regardless of whether silver is provided in the form of silver ions or as a topical composition (silver nitrate solution, silver sulfadiazine cream, or the like), its beneficial effects are manifested primarily at the treated surface and immediately adjacent tissues, and are limited by the achievable tissue concentration of silver ions. Despite the availability of numerous techniques for the delivery of silver and silver compounds in vitro and in vivo, there remains a need for a delivery system that is capable of supplying clinically useful concentrations of silver ions to a treatment site without the need for adjuvant electrical stimulation.

None of the available metallic ion treatment devices provide an efficient and convenient means to restore the homeostatic electromagnetic environment for areas of wounds. They also do not provide for maximum surface area for release of metallic ions. In addition, the prior art does not address the need to regulate the moisture content of a wound without manually changing the dressings, or applying liquids or medicants. This is true in part because of the belief that a wound dressing must serve as a microbial barrier and prevent the movement of fluids from the wound exudates. The currently available treatments for wounds prevent microbial contamination by providing a physical barrier which must be manipulated and interrupted as part of the treatment process. Such activities allow for microbe contamination and interrupt the healing process.

It is believed that wound healing occurs with maximum speed and efficiency when the wound is maintained in a moist condition without excessive wetness or dryness. Wounds have variable hydration needs based upon the type of wound and the phase of healing. There are many types of wound dressings on the market to meet the differing needs of different types of wounds, however, none provide for the regulation of the fluid content of the wound.

What is needed is a means for treating wounds that addresses the above problems, and provides a functional anti-microbial barrier, allows for regulation of the moisture content of the wound, and aids in maintaining the transepithelial potential across the epithelium.

SUMMARY OF THE INVENTION

The present invention relates to compositions and methods for making moisture regulating wound dressings that can aid in restoring the transepithelial skin potential, maintain a moist wound healing environment, create a functional microbial barrier, reduce microbial bio-burden of the wound, and aid in reducing pain.

The present invention comprises wound dressings and methods of using such dressings. Wound dressings of the present invention comprise one or more layers of materials. One of the layers can be a layer comprising metal-plated fibers, foams or combinations of fibers and foams. This layer, referred to as the conductive layer, comprises fibers, foams or a combination of fiber and foams that have from approximately 0% to approximately 100% of the surface or surfaces of the fiber or foam covered with a metal plating, and all ranges therebetween. Fibers or foams that do not have metal plating are referred to as nonconductive and fibers or foams with metal plating are referred to as conductive.

Medical devices of the present invention can comprise a second layer that is an absorbent layer. Medical devices of the present invention can comprise a third layer that is a moisture control layer, which may be impermeable to gases or liquids or may have apertures therein that allow transmission of differing materials such as gases, liquids or microbial or environmental contaminants.

Preferably, the at least one conductive layer can be placed in contact with a wound. At least a portion of the conductive layer comprises substrates coated with a coating of a metal. Fibers include but are not limited to alginates, chitosans, polymers, synthetic and naturally occurring fibers. Fibers may vary in composition and three dimensional structure. A preferred conductive layer comprises a plurality of fibers wherein at least one fiber comprises a three dimensional structure and the fiber is substantially coated with a metal. Another preferred conductive layer comprises a polymeric foam structure wherein at least a portion of the foam surfaces are substantially coated with a metal, or the layer comprises a combination of fibers and foams. The plurality of fibers or foams within the conductive layer comprise at least one fiber or foam, having its surfaces coated with metal and include fibers or foams that are shaped to provide a spontaneous movement of fluids such as capillary action or wicking of fluids. Such fibers or foams are designed with grooves or channels along the longitudinal axis of the fiber or foam and these channels serve as ducts to move fluids, store or trap substances and provide a large surface area for a given denier per fiber or surface area of a foam.

Preferably, additional layers of the dressing include at least one absorbent layer and at least one moisture regulation layer having a plurality of apertures disposed primarily in the moisture regulation layer. The apertures may vary in size from a layer with no apertures to apertures in a size range that is occlusive to liquids but not to gases, to a size range that allows liquids and gases to pass through, to a size that is open to microbes, such as bacteria, viruses, fungi, parasites, and environmental contaminants.

An additional aspect of the invention relates to wound dressings that provide for a capacitive effect formed by the alternation of conductive layers of fiber with non-conductive layers.

Another aspect of the invention relates to wound dressings having a plurality of layers arranged according to the ratio of conductive to nonconductive fibers comprising each layer. Additional aspects of the invention relate to various configurations of the functional shape of the novel dressings. Another aspect of the invention relates to methods of using the novel dressings to treat wounds in a human or an animal. Further aspects of the invention relate to methods of making the novel dressings.

BRIEF DESCRIPTION OF THE DRAWINGS

The invention is illustrated in the drawings in which like reference characters designate the same or similar parts throughout the figures of which.

DETAILED DISCLOSURE OF THE INVENTION

Figure 1:
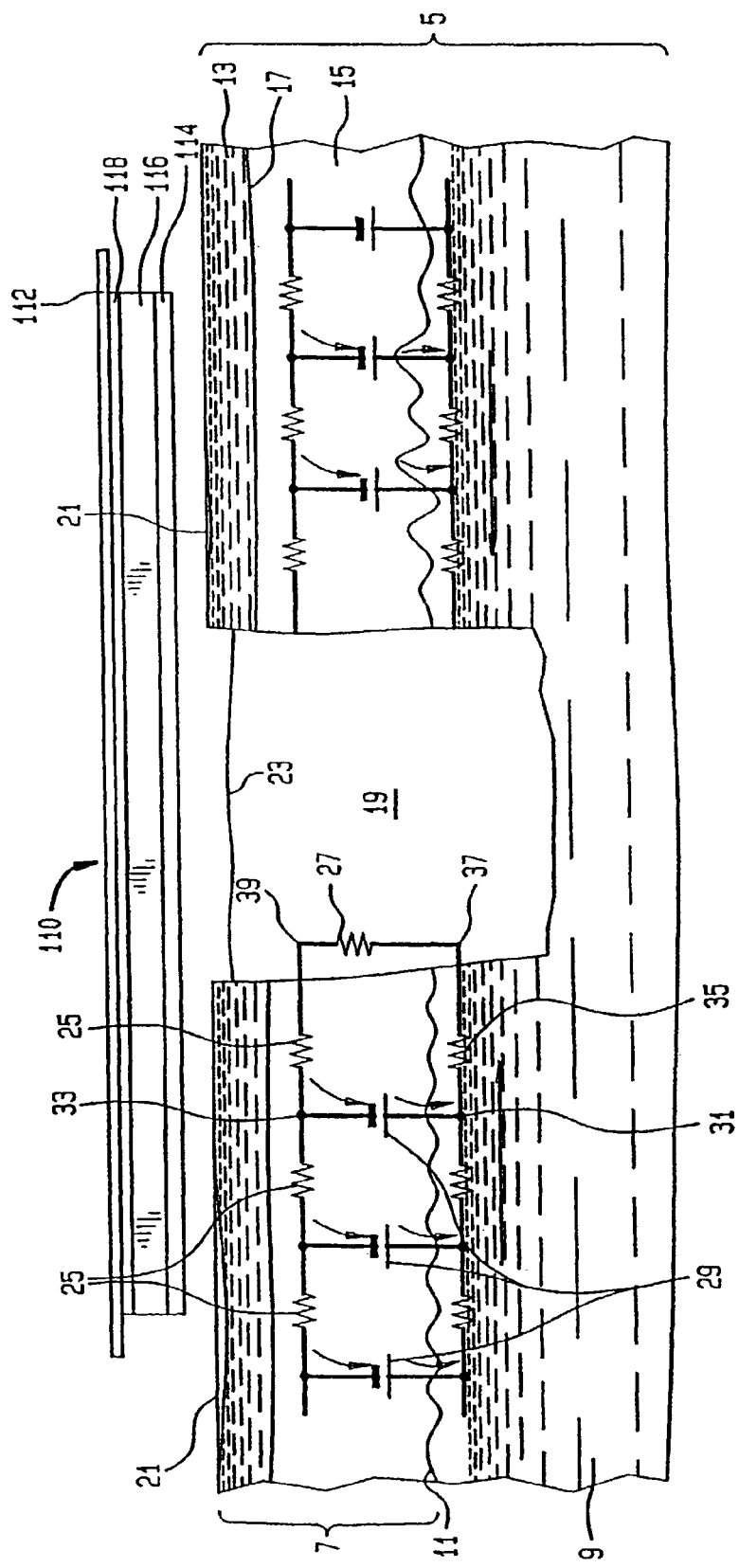
FIG. 1 is a schematic depiction of a cross-section of wounded mammalian skin with a dressing in accordance with an embodiment of the present invention positioned over the wounded area.

The present invention comprises compositions for medical devices and methods for the treatment of wounds in a human or animal using the compositions and medical devices. Though not wishing to be bound by any particular theory, it is believed that the wound dressings aid in healing by (1) assisting with restoration of the transepithelial skin potential; (2) creating an anti-microbial barrier to environmental pathogens without restricting the passage of liquids and gases; (3) aiding in the regulation of the moisture content at the wound surface and of the dressing and allowing fluids to be manually added or removed, or to be added or removed by means of a secondary dressing; (4) allowing medicants or liquids to be added to the wound dressing without disturbing the wound surface; and (5) aiding in the reduction of pain originating from the wound. The present invention comprises methods of treating wounds and methods of making the novel dressings.

For purposes of the invention, the term "wound" refers to any wounds, internal or external to the body of a human or animal including, but not limited to, lesions, rashes, blisters, pustules, abrasions, hives, dermal eruptions, partial thickness wounds, partial thickness burns, incisions, skin graft sites, skin donor sites, lacerations, Stage I-IV dermal ulcers, venous stasis ulcerations, pressure ulcerations, arterial insufficiency ulcerations, diabetic ulcers, decubitus ulcers, organ lacerations, organ abrasions, organ tears, or external and internal surgical wounds. For purposes of the invention, the term "organ" refers to any part of the body of a human or animal having a special function including, but not limited to, bone, muscle, skin, heart, eyes, liver, kidney, vascular system, lungs, reproductive organs, and the like. The term wound can also-refer to any abnormal condition of an organ of a human or animal that results from mechanical or physiological events or conditions.

As used herein, the terms "fiber" or "fibers", "foam" or "foams" are interchangeable. Though the terms denote differently formed materials, where one of the terms is used, the other or the plural of either is intended.

Dressings are provided that control the moisture levels of the wound surface including controlling the moisture loss, altering the aperture or slit configuration of the dressing; altering the materials of the wound contact layer; altering the absorbent characteristics of one or more absorbent layers. Absorbent layer materials include, but are not limited to, hydrogels, chitins, alginates, polyurethane foams, acrylates, hydrocolloids, collagens, and cellulosic materials.

The present invention comprises medical devices comprising layers comprised of conductive material, absorbent material and moisture retention material wherein the layers can mean at least one layer, at least two layers, at least three layers, at least four layers, at least five layers, at least six layers, at least seven layers at least eight layers, at least nine layers, at least ten layers, and more.

Figure 7:
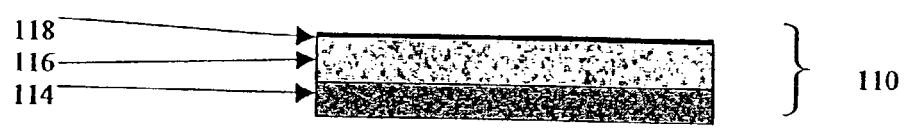
FIG. 7 depicts a cross-section of FIG. 6 illustrating one aspect of a wound dressing.

In a first embodiment of the invention as illustrated in FIG. 7, the wound dressing comprises at least one conductive layer, at least one absorbent layer positioned adjacent the conductive layer or adjacent to a moisture regulation layer, and at least one moisture regulation layer positioned adjacent to the absorbent layer or adjacent to the conductive layer and comprising a plurality of apertures of varying sizes disposed substantially throughout and in the moisture regulation layer.

In devices of the present invention, at least a portion of the conductive layer comprises fibers or foams coated with a metal, wherein in a range of from approximately 0% to approximately 100% of the surfaces of the fibers or foams are coated. The fibers or foams may have areas of the length of the fiber or foam that are coated in a range of from approximately 0% to approximately 100% of the surfaces. For example, in a 3 inch fiber, the first inch is uncoated, the surface or surfaces of the second inch is 100% coated, and the third inch is uncoated.

Uncoated or non-conducting fibers and foams, including but not limited to alginates, chitosans, polymers, synthetic and naturally occurring fibers or foams may be placed in the conductive layer. The metal-plated fibers and foams and the nonconductive fibers and foams vary in composition and may or may not have a functional three dimensional structure used for movement of fluid. A layer may include, but is not limited to a plurality of fibers wherein at least one fiber is coated with a metal, or a layer may include a polymeric foam wherein at least a portion of the foam comprises a three dimensional coating of a metal, and preferably, a uniform coating of metal. The plurality of fibers where in at least one fiber comprises a three dimensional coating of a metal may also include fiber or foam shapes that provide movement of fluids, such as capillary action or wicking of fluids. The fibers or foams are designed with grooves or channels along the longitudinal axis of the fiber or foams and serve as ducts to move fluids without a pumping means, such as in capillary action, store or trap substances and provide a large surface area or an active surface area for a given denier per filament or foam. For purposes of the invention, the term "three dimensional coating" refers to the circumferential, concentric, uniform coating of all the surfaces of a fiber or foam which may be the entire length of the fiber or foam or may comprise one or more coated sections of the fiber or foam. Preferably, during treatment, the dressing can be positioned with the conductive layer in contact with a wound, or with the absorbent layer in contact with the wound.

The base substrate that is coated with a metal to form the conductive layer can be any biocompatible, flexible, synthetic or natural material that can be formed into a film, fiber, foam, web, or any configuration capable of supporting a metal coating and combinations of such forms. The base substrate materials can include, but is not limited to carbon, polyamide, glass, KEVLAR®, acetate, flax, olefin, polyethylene, rubber, saran, spandex, vinyl, polyester, silk, wool, rayon, cotton, cellulose or combinations thereof. Configurations include fibers, films, foams or webs comprising blends, composite materials, or multi-component fibers, either woven, knitted or non-woven. Some individuals may have a topical hypersensitivity to certain fiber materials, and the base fiber is preferably non-allergenic or hypoallergenic. It is to be understood that for purposes of illustration, the discussion refers to fibers for the conductive aspect of the invention, but can also include conductive foams.

A preferred material for making fibers or foams used in the present invention is any materials that has a nitrogen group or a similarly functional group capable of being sensitized, that is available for sensitizing the material for autocatalytic metal plating. If the material does not have a nitrogen group on the surface of the material, then a layer of different material, which provides a nitrogen, can be coated on the foam or fiber prior to sensitizing. For exampler, cross-linked polyethylene fibers are coated with polyamide to provide a nitrogen group on the surface of the fibers. The polyamide-coated fiber is then sensitized for autocatalytic metal plating. Compositions and methods for sensitizing materials for autocatalytic metal plating are known to those skilled in the art and include, but is not limited to, tin chloride. After sensitizing the polyamide-coated fiber, a metal, such as silver, is autocatalytically plated onto the fiber. The autocatalytic metal plating preferably provides a uniform metal coat to the sensitized section of the fiber. The preceding description also applies to metal plating of a foam.

Under optimum conditions, the conductive layer (114), when moistened, can be electrically conductive, non-adherent, liquid and gas permeable, porous, and anti-microbial. The conductive layer may contact the surface of the wound and the surface of normal tissue surrounding the wound. Ideally, the composition of the conductive layer comprises a plurality of fibers, wherein at least one fiber is uniformly and concentrically coated with a metal or metal alloy so that the coating is three dimensional and covers all surfaces of the fiber. Ideally also, the conductive layer comprises a polymeric foam wherein the surface is uniformly and concentrically coated with a metal or metal alloy so that the coating is three dimensional and covers all surfaces of the foam For purposes of the invention, all or part of the fiber or foam can be coated three-dimensionally. Preferably, all or a plurality of the surface area of the fibers or foam of the conductive layer (114) are auto-catalytically plated with metal to allow for a uniform, three dimensional coating of the metal or metal alloy and provide the maximum surface area for release of metallic ions. The anti-microbial activity of released metallic ions and the metallic surface function as a microbial barrier, and aid in preventing the migration of microbes from the surrounding environment to the wound surface, while at the same time allowing fluids and gases to pass freely.

For purposes of the invention, any metal or metal alloy capable of being plated onto a substrate to form a conductive layer can be used. Metal elements suitable for the present invention include, but are not limited to, platinum, copper, gold, nickel or silver, and/or binary alloys of platinum, nickel, cobalt or palladium with phosphorus, or binary alloys of platinum, nickel, cobalt or palladium with boron. In one preferred aspect of the present invention the metal is silver. For purposes of explanation, silver is used to describe the invention, though it can be substituted with any other metal or metal alloy.

One embodiment of the present invention comprises devices having a conductive layer that comprises areas of the layer having metals that provide a permanent or semi-permanent magnetic field. In a conductive layer, if a current is generated by the movement of metal ions, particularly under moist conditions of fluid flow, an electric field and a transitory magnetic field are generated. By providing areas of the layer with particular metals, such as isotopes of cobalt, a semi-permanent or permanent magnetic field can be provided to the wound site. This magnetic field is not dependent on the fluid flow or generation of a current, but provides a steady magnetic field. Though not wishing to be bound by any particular theory, it is believed that a magnetic field held in place at a wound aids in the healing processes.

Ideally, the metallic silver used for the invention is of high purity, preferably from about 99.0% to about 99.6% pure, although lower purity levels can also function. It is believed that high purity reduces the likelihood that contaminants or undesirable ions may contact or penetrate the wound or skin.

Preferably, the substrate can be in the form of fibers. The range of denier of the fibers can be from about 0.0001 denier to about 10,000 denier, preferably from about 1.0 denier to about 1000 denier, and more preferably from about 5 denier to about 300 denier. The various cross-sectional shapes that may be imparted to individual fibers are known to those skilled in the art, and include, but are not limited to, round, oval, kidney-bean, dogbone, flat, tri-lobal, and multi lobal. Advantageously, a multi-lobal fiber such as the 4DG fiber commercially available from Fiber Innovation Technology Inc of Johnson City TN can increase the surface area by 250% to 300% compared to round fibers. Fiber configurations that are capable of spontaneously transporting water on their surfaces are also available and include a number of fibers similar to the 4DG fiber. In general, while not wishing to be bound to any particular theory, it is believed that the greater the surface area of the fiber, the greater the surface area of metallic plated fibers, forming an active surface area, which can result in greater release of metallic ions and a more effective dressing.

Individual fibers may be fabricated into several different types of yarns including, but not limited to, spun yarns, filament yarns, compound yarns, fancy yarns, and combinations thereof. Fibers can be configured into tow and floc and can be provided in the form of staple or bulk continuous filament. The filament and compound yarns that exhibit multiple longitudinal filaments are preferred. It is believed that the greater the continuity of the yarns, the greater the potential for excellent conductivity when plated. Fibers and/or yarns can be assembled into fabrics, including but not limited to, woven fabrics, twisted and knotted fabrics, knit fabrics, non-woven fabrics, and compound/complex fabrics. It is proposed that the total surface area of the fibers that compose the filaments, fibers, yarns or fabric is a variable in determining conductivity as well as passive metal ion release into aqueous fluids It is preferable that the autocatalytically metal-plated surfaces have a broad range of resistance from about 1,000 kiloohms/in$^2$ to about 0.0001 ohms/in$^2$, a middle range from about 10 kiloohms/in$^2$ to about 0.001 ohms/in$^2$ and an optimal range from about 10 ohms/in$^2$ to about 0.1 ohms/in$^2$. It is believed that resistance decreases with increasing numbers of plies or fibers within a layer. Preferably, beyond four plies of conductive fabric, the resistance decrease may become non-appreciable from a clinical point of view, although the resistance may continue to decrease with additional layers. The preferable upper limit of the number of plies of conductive fabric can be about ten. Cost, thickness, composition, fiber density and weave structure and other factors may also be considered in selecting the number of plies. A more dense fabric design may need only one ply to achieve the same resistance measurement as a fabric having more than one ply of a highly absorbent material that is less dense. The reduction of the resistance of the conductive layer can relate to the manner in which the fabric is plated and secondarily to how the layer is constructed. It is believed that fabrics having continuous fibers or fibers melted together can appear to have lower resistance with greater continuity of the metallic layer. It is thought that the larger the surface area of fiber contact, the better the conductivity and the lower the resistance. It is also believed that the polymeric foam materials that are autocatalyticly metal plated provide a large surface area of metallic silver with low resistance and high conductivity.

Figure 3A:
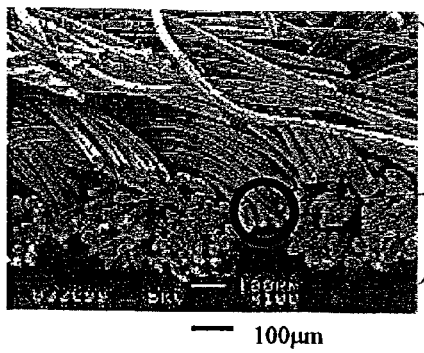
FIG. 3A is a representative cross-section of polymeric autocatalytic plated fibers on a non-conductive substrate.
Figure 3B:
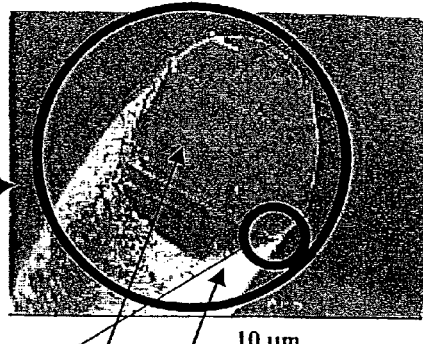
FIG. 3B is a cross-section of one polymeric autocatalytic plated filament from FIG. 3A.
Figure 3C:
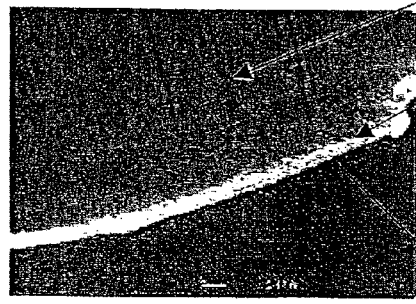
FIG. 3C is a portion of the cross-section of one polymeric autocatalytic plated filament of FIG. 3B.
Figure 3D:
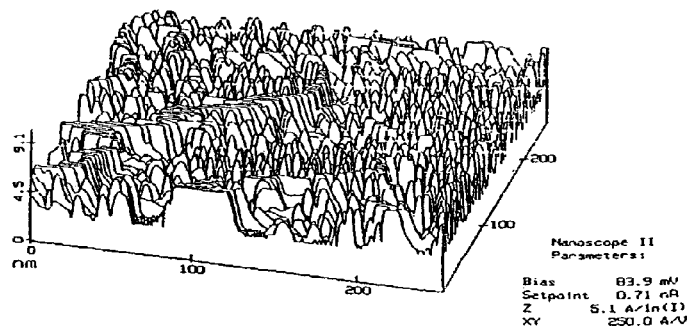
FIG. 3D is an illustration of an enlargement of the metallic surface of a polymeric autocatalytically plated filament representing approximately 62 µm$^2$.
Figure 17:
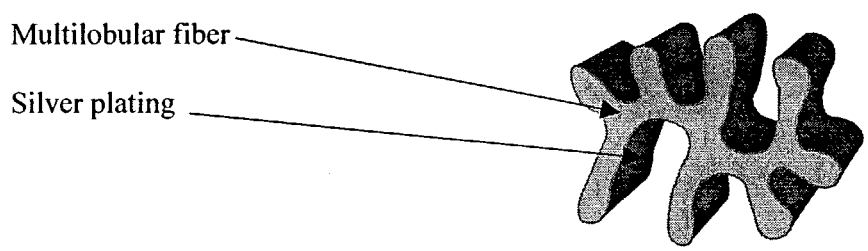
FIG. 17 is a cross-section of an autocatalytic metal plated filament that provides spontaneous movement of fluids

A preferred aspect of the conductive layer is a non-conductive polymeric filament/fiber substrate that has been autocatalytically plated with silver. FIG. 3A is a representative cross-section of a polymeric autocatalytically plated fabric composed of multifilaments formed into yarns and knitted into a fabric. FIG. 17 represents a multilocular fiber that is uniformly metal plated on all surfaces. All filaments, (40) are three dimensionally coated with a uniform layer of metal (41). FIG. 3B represents as cross-section enlarged detail of FIG. 3A showing the uniform metallic coating (41) of one filament (40). FIG. 3C is an enlarged detail of FIG. 3B showing the uniformity of metallic plating covering the polymeric substrate. FIG. 3D is an enlargement of the metallic surface of a polymeric autocatalytically plated filament representing approximately 62 μm$^2$ of surface area.

Figure 15:
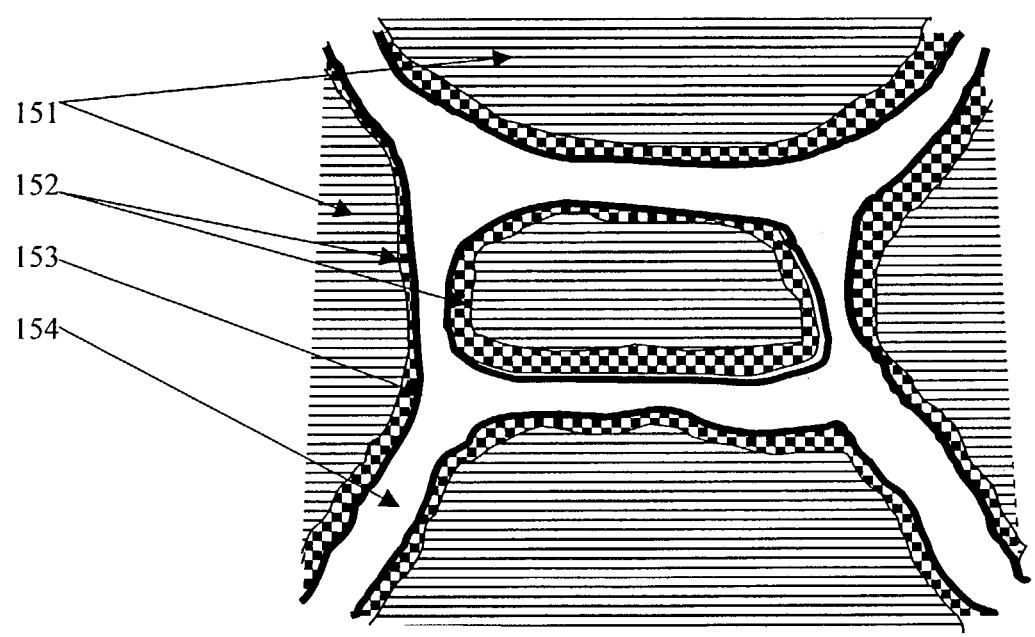
FIG. 15 is a cross-section of a two-layer autocatalyticly metal plated foam.
Figure 16:
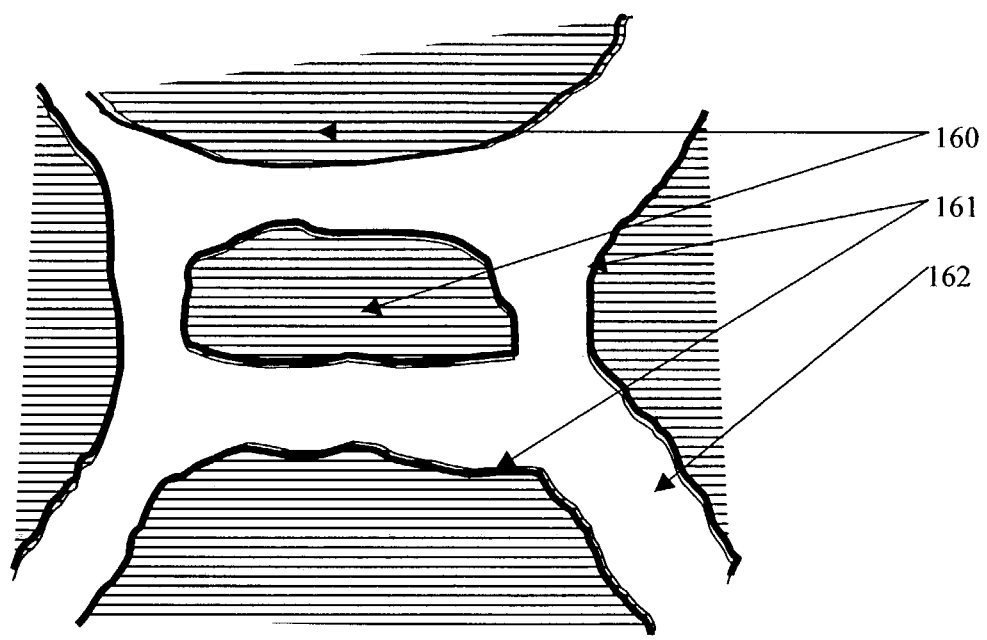
FIG. 16 is a cross-section of a one-layer autocatalyticly metal plated foam.

Another preferred aspect of the conductive layer is a non-conductive polymeric foam substrate that has been autocatalytically plated with silver. FIG. 15 and FIG. 16 are representative cross-sections of a polymeric autocatalytically plated foam. FIG. 15 represents a polymeric foam substrate (151) with a second polymeric foam coating (152) that is in turn autocatalytically metal plated (153). FIG. 16 represents a polymeric foam substrate (160) that is autocatalytically metal plated (161). Open spaces are represented in FIG. 15 and FIG. 16 by 162 and 154. All metal plated surfaces are three dimensionally coated with a substantially uniform layer of metal.

FIGS. 3A, 3B, 3C and 3D demonstrate that the actual surface area of metallic silver exposed to a liquid can be significantly greater than the geometric surface area of the fabric. Assuming the surface of the plated metal is smooth, the ratio of geometric surface area to actual surface area can have a range from about 1:2 to about 1:10,000, from about 1:10 to about 1:1000, from about 1:10 to about 1:500, 1:20 to about 1:500, from about 1:20 to about 1:250, from about 1:10 to about 1:250, from about 1:10 to about 100 and an optimal ratio range from about 1:20 to about 1:100. Taking into consideration FIG. 3D, it is believed that the actual surface area can be extended by a multiple of between about 10 and about 1000 above the calculated smooth surface area. Even though a uniform coating is preferred, there may be applications wherein non-uniform coatings are preferable.

The thickness of the uniform coating can vary from about 0.1 micrometers to about 2.0 microns, from about 0.1 microns to about 1 micron, from about 0.1 microns to about 1.5 microns, preferably from about 0.2 microns to about 1.5 microns. Preferably, the thickness of metal coating is directly correlated with the percentage of weight of silver plated to the weight of the fabric without silver plating. The amount of coating can vary from about 5% to about 40% by weight, from about 5% to about 30% by weight, from about 5% to about 20% by weight, from about 5% to about 10% by weight, from about 10% to about 30% by weight, from about 10% to about 25% by weight, from about 10% to about 20% by weight, from about 15% to about 30% by weight, more preferably between about 15% to about 22% by weight. While not wishing to be bound to any particular theory, it is believed that filaments and fibers that are uniformly plated may have the greatest electrical conductance and the lowest electrical resistance. Preferably, the maximum conductance and minimum resistance can be directly correlated. Preferable for the invention is a plating thickness between about 0.2 to about 1.5 microns, and between about 14% to about 22% of the weight of the plated fabric composed of metallic silver. Most preferably, the conductivity of the plated fiber can significantly decrease when the percent of weight of plated fabric falls below about 10%. Silver-coated fibers suitable for use in the present invention are commercially available from Conductive Specialty Fabrics Manufacturing, Lakemont, Ga.

The dressings can also comprise at least one absorbent layer (116) that functions primarily as a reservoir for receiving and storing wound exudates or other fluids. The absorbent layer may provide a source of moisture in wounds with minimal fluid drainage or exudate by receiving and holding fluids that are provided from an external source through a plurality of apertures in layers superficial to the absorbent layer. The absorbent layer may contain any number of layers of conductive metal plated fibers uniformly mixed with non-conductive fibers. The absorbent layer can also comprise only non-conductive fibers or material. For purposes of the invention, non-conductive fibers or material are any fibers or materials that are not coated with a metal or metal alloy and are not capable of conducting an electrical charge or releasing ions.

The at least one absorbent layer can comprise any absorbent material, and the dressing can comprise any number of absorbent layers positioned adjacent to any other layer of the dressing. Advantageously, the absorbent layer can be positioned adjacent to the moisture regulation layer. In another aspect of the invention, the absorbent layer can be positioned between the conductive layer and the moisture regulation layer.

Absorbent materials suitable for the absorbent layer comprise any biocompatible synthetic or natural absorbent material known in the art including, but not limited to, a foam, a sponge or sponge-like material, cellulosic materials, cotton, rayon, polyvinyl alcohol, polyvinyl acetate, polyethylene oxide, polyvinyl pyrrolidon, polyurethane hydrocolloids, alginates, hydrogels, hydrocolloids, hydrofibrils, collagens or any combinations thereof.

Figure 10:
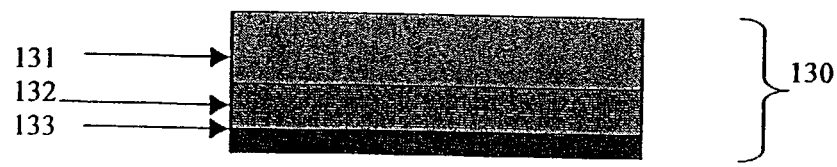
FIG. 10 depicts a cross-section of an alternative aspect of an absorbent layer.

In one aspect of the absorbent layer, layers of metal plated conductive fibers and non-conductive fibers can be uniformly distributed throughout at least one, and preferably more layers. Alternatively, metal or metal alloy plated and non-conductive fibers can be uniformly distributed throughout the absorbent layer. It is contemplated as being within the scope of the present invention to have layers of absorbent material of differing ratios of metal plated conductive fibers to non-conductive fibers as well as differing thicknesses of the layers. The layers may be in the form of woven, knitted or non-woven fabrics. The absorbent layer (130) demonstrated in FIG. 10 is composed of layers (131, 132, and 133) of the absorbent material with varying ratios of metal plated conductive fibers to non-conductive fibers and varying layer thicknesses. As the concentration of metal plated conductive fibers increases and the concentration of non-conductive fibers decreases, the ratio of metal plated conductive fibers to non-conductive fiber increases. As the concentration of metal plated conductive fibers decreases and the concentration of non-conductive fibers increases, the ratio of metal plated conductive fibers to non-conductive fibers decreases. In a given layer, the ratio of metal or metal alloy plated conductive fibers to non-conductive fibers can be from about 1:100 to about 1:0, from about 1:75 to about 1:0, from about 1:60 to about 1:0, preferably from about 1:50 to about 1:0, from about 1:40 to about 1:0. from about 1:30 to about 1:0 and more preferably from about 1:25 to about 1:0. In the situation wherein the layers comprise about 100% conductive metal fibers, the ratio would be about 1:0. The ratio of conductive metal or metal alloy plated fibers to non-conductive fibers, although constant within a given layer, may vary from layer to layer. Advantageously, there can be an increasing ratio of conductive metal plated fibers to non-conductive fibers the closer the layer is to the wound. Thus, there can be a decreasing concentration gradient of conductive metal fibers in each subsequent layer further from the wound site. Concentration gradients of mixed fibers can be made according to processes known to those of ordinary skill in the art.

The thickness of layers (131, 132 and 133) of FIG. 10 may be similar or may vary. Ideally, the thickness of the layers increases as the distance from the wound surface increases. In an additional preferred aspect, the increasing thickness of the layers occurs in a ratio of the fibonacci numbers (i.e. 1,2,3,5, 8,13,21 . . . ).

Figure 12:
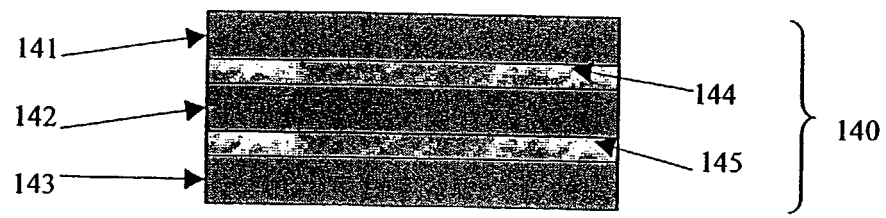
FIG. 12 is an illustration of a cross-section of an alternative aspect of a wound dressing.

In another aspect of the absorbent layer, shown in FIG. 12, a multilayer structure (140) comprises conductive layers (141, 142, 143), with a non-conductive layer (144) interposed between conductive layers (141) and (142), and a non-conductive layer (145) interposed between conductive layers (142) and (143). The composition of conductive layers may be similar and formed from conductive metal plated fibers or a mixture of conductive metal or metal alloy plated fibers and non-conductive fibers in the form of a woven, knitted or non-woven fabric. The mixture of conductive metal or metal alloy plated fibers and non-conductive fibers can be uniform in each layer and may have a decreasing ratio of conductive plated metal fibers to non-conductive fibers the closer the layer is to the wound surface. A layer of non-conducting, flexible material can be positioned between the conductive layers. In one aspect, the non-conductive layers can be composed of impermeable or semi-permeable materials with apertures disposed substantially throughout. In FIG. 12, the use of the alternating conductive metal plated fiber layers (141, 142 and 143) and non-conductive fiber layers (144 and 145) can create a capacitor-like laminate.

The moisture regulation layer (118) shown in FIG. 7, can be any biocompatible semi-permeable or impermeable material for limiting the evaporation of moisture from the absorbent layer and the wound surface. At least one moisture regulation layer (118) can be positioned adjacent to the conductive layer or adjacent to the absorbent layer of the dressing. Advantageously, the moisture regulation layer can be positioned adjacent to the absorbent layer and can be fixedly attached or removably attached for easy removal and replacement.

The moisture regulation layer not only controls the rate of moisture evaporation from the absorbent layer, but also functions as a physical barrier to the penetration of microbes from the surrounding environment. The rate of moisture evaporation from the moisture regulation layer is related to the size of the apertures. Very small aperture sizes allow the release of gases but not liquids, while larger aperture sizes allow the release of gases and liquids. Even larger-sized apertures allow the entry of microbes such as bacteria and fungi and environmental contaminants. Though not wanting to be bound by any particular theory, it is theorized that the placement of apertures larger than the size of microbes (such as bacteria and fungi) in this layer runs counter to the prevailing teaching that a physical barrier must be provided to prevent the penetration of microbes from the surrounding environment. The present invention substitutes the traditional physical anti-microbial barrier to microbial penetration with a functional anti-microbial barrier through application of the anti-microbial metal plated fibers. The functional anti-microbial barrier of anti-microbial metal plated fibers has allowed the apertures to be placed in the moisture regulation layer without fear of compromise of the physical barrier to environmental microbial contamination of the wound.

The moisture regulation layer can be a film, fabric or foam. Some preferred materials include, but are not limited to, polyurathanes, polyolefins such as linear low density polyethylene, low density polyethylene, ethylene vinyl acetate, vinylidene, chloride copolymer of vinyl chloride, methyl acrylate or methyl methacrylate copolymers and combinations thereof. A preferred polymeric material is polyurethane, either as a film or as a polyurethane foam. The polyurethane may be an ester or ether based polyurethane. Materials suitable for a foam moisture regulation layer can be any semipermeable or impermeable natural or synthetic compound including, but not limited to, rubber, silicon, polyurethane, polyethylene polyvinyl, polyolefin, or combinations thereof.

Alternatively, the moisture regulation layer, (118), may be a transparent elastomer film for visual inspection of the moisture status of the absorbent layer dressing. Preferably, the film can have a thickness from about 10 µm to about 100 µm, from about 10 µm to about 90 µm, from about 10 µm to about 80 µm, from about 15 µm to about 100 µm, from about 15 µm to about 90 µm, from about 15 µm to about 80 µm, from about 15 µm to about 70 µm, from about 20 µm to about 100 µm, from about 20 µm to about 90 µm, and more preferably from about 20 µm to about 80 µm. In some materials, a thickness below 10 µm may result in poor mechanical strength or handling properties and a thickness of the transparent elastomer film exceeding about 100 µm may result in poor flexibility and comfort to the body. Preferably, the moisture regulation layer has an MVTR of from about 300 to about 5,000 grams/meter$^2$/24 hours, preferably from about 800 to about 2,000 grams/meter$^2$/24 hours. The moisture regulation layer can be laminated to the absorbent layer by methods well recognized in the art.

Figure 6A:
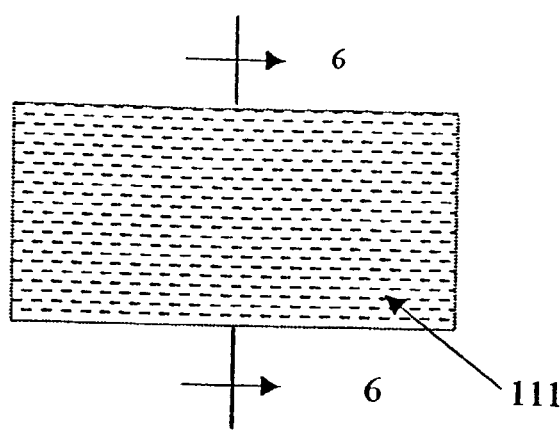
FIG. 6A is an illustration of a possible geometric shape for apertures.
Figure 6B:
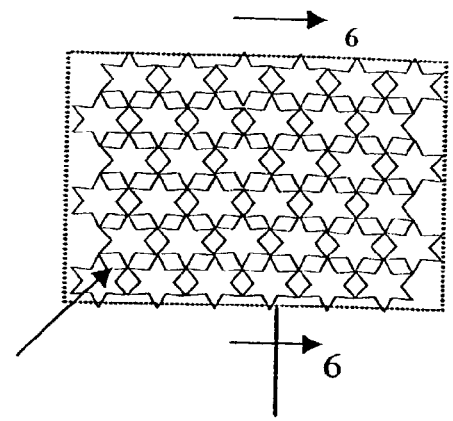
FIG. 6B is an illustration of a possible geometric shape for apertures.

To regulate the moisture level of the wound dressing, apertures, (111) as illustrated in FIGS. 6A and 6B, are disposed in the moisture regulation layer. The apertures can be any geometric shape having curved lines, straight lines, or a combination thereof. Shapes include, but are not limited to, slits, stars, oval, circles, semicircles, squares, rectangles, polygons or any combination thereof. The apertures can be disposed randomly or in uniform patterns, groups, or bunches. Such apertures allow for addition or removal of liquids from the absorbent layer. In a method of use for wound treatment, the apertures would allow the wound to be bathed by dispensing liquids, medicaments, cleansing or treating agents, without removing the dressing.

The size of the apertures can improve the regulation of the moisture level of the absorbent layer, the conductive layer, and the surface of the wound. It is believed that the regulation of the moisture level in the wound provides benefits such as the release of anti-microbial metallic ions from the conductive metal plated fibers and fabrics and enhances the analgesic effect, improves conductivity of the conductive metal plated fibers, and assists with restoration of the electrical potential of the wound site. As a result, while not wising to be bound to any particular theory, it is believed that the cellular growth and regeneration is enhanced, expediting the healing of the wound.

Figure 13:
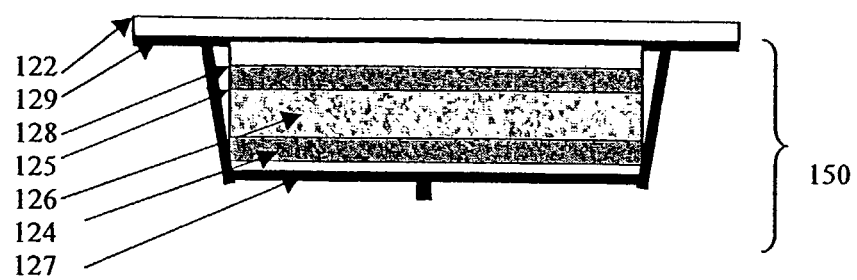
FIG. 13 illustrates a cross-section of an alternative aspect of an island wound dressing.
Figure 14:
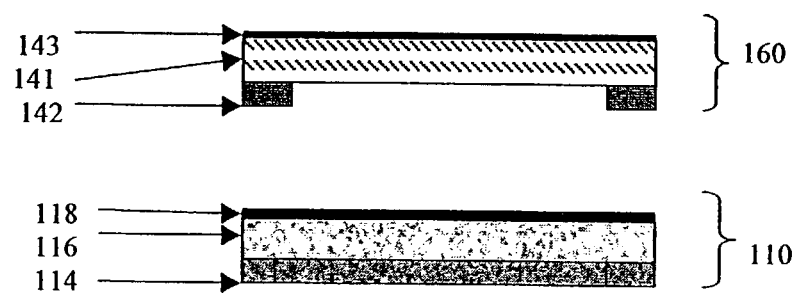
FIG. 14 is an illustration of a cross-section of a secondary wound dressing.

Large apertures in general can cut through one layer or multiple layers. The apertures are positioned to allow direct liquid and medicants to be administered from the external environment to the absorbent layer. The apertures (111) of the multilaminate wound layer dressing (110) of FIGS. 7 and 14 are cut through the moisture regulation layer and are not cut through the absorbent layer or other layers between the moisture regulation layer and the surface of the wound. The apertures (111) of the multilaminate island wound dressings, (120) of FIG. 9 and FIG. 13 (150), are cut through the backing sheet, the adhesive layer, and the moisture regulation layer. With respect to the island wound dressing, (120) of FIG. 9, the aperture pattern is limited to the area over the moisture regulation layer. The apertures in the island dressing of FIG. 9 extend through a back sheet layer (112), adhesive layer (119) and moisture regulation layer (118).

Advantageously, a semipermeable or impermeable moisture regulation layer can be laminated to an absorbent layer such that, regardless of the pattern of apertures, delamination of the moisture regulation layer from the absorbent layer does not occur. The apertures allow for movement of fluids or medicants to and from the absorbent layer. The regulation of moisture content can be controlled by application of fluids via a bulb syringe or similar application device, or alternatively by a secondary dressing (120) as shown in FIG. 14.

In alternative aspects of the invention, it is helpful to provide a moisture regulation layer that is releasably or removably attached to an absorbent layer or a conductive layer of the dressing. This allows for the removal and replacement of the moisture regulation layer without disturbing the wound. The moisture regulation layer can be affixed to the adjacent layer by any artful means that will allow for quick removal from the absorbent layer including, but not limited to, adhesives, knitting techniques, lamination, or a combination thereof.

The layers of the devices of the present invention may or may not be attached to each other or be provided as a component of another structure. For example, a metallic, conductive layer, made from metal-plated fibers, is applied directly to the affected site, such as a wound. A foam is then applied as a second layer above the site to provide the absorbent layer. A moisture retention layer is then placed on the surface of the foam farthest from the affected site to control the moisture content of the affected site. In another example, a two or three layer bandage, comprising at least a conductive layer as the first or second layer closest to the affected site, is provided wherein the layers are attached to one another.

In any aspect of the present invention, the conductive layer can be positioned in the dressing for placing in direct contact with the wound surface upon application of the dressing to the wound. Alternatively, the absorbent layer can be positioned in the dressing for placing in direct contact with the wound surface upon application of the dressing to the wound. For treatment of internal wounds, for example for treating surgical wounds on internal organs, the conductive layer or absorbent layer can also be positioned for placement in direct contact with the wound surface upon application of the dressing to the wound.

The various aspects of the wound dressings of the present invention can comprise an optional adhesive layer positioned between any adjacent layers, or advantageously, the adhesive layer can be the top layer of the dressing. Useful adhesives include those known in the wound dressing art, including but not limited to, rubber-based, acrylic, vinyl ether and hydrocolloid pressure sensitive adhesives. Conveniently, anti-microbial agents can be added to the adhesive material.

The wound dressings of the present invention can be formed into any of a number of possible shapes, patterns or geometries, depending upon the application and topography of the wound or application site. Any aspect of the wound dressing of the present invention can be manufactured in a variety of shapes and configurations. For example, configurations can include, but are not limited to, compressive wraps, tampons, tubular, roll gauze, pads of varying sizes and shapes, island dressings, strip dressings, dressings for dental applications, rectal dressings, vaginal pads, surgical packing or dressings, or any combination thereof.

Figure 11:
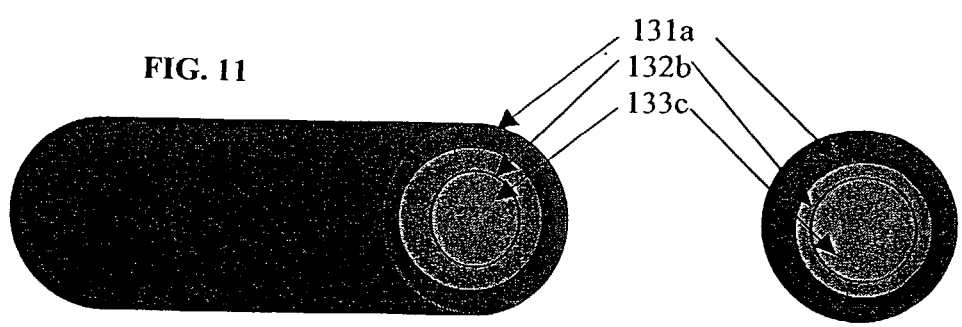
FIG. 11 represents a cross-section of an alternative aspect of a wound dressing.

FIG. 11 shows a tubular configuration of the wound dressing. The tubular configuration may be composed of one or more layers. The layers can be composed of about 100% metal plated fibers or foam or a ratio of conductive metal fibers or foam to non-conductive fibers or foam. The tubular configuration can take the shape of a wrap for circumferentially placing around an area to be treated. The distribution of conductive metal fibers and non-conductive fibers in each layer can be uniform. The conductive metal plated fibers of layers 131*a*, 132*b* and 133*c* represent an increasing ratio of conductive metal plated fibers to non-conductive fibers as the layers are positioned closer to the wound contact surface. The layers can be in the form of a woven, knitted or nonwoven fabric. The tubular configuration of this aspect of the invention can be used in dressing applications including, but not limited to, a vaginal, mouth, nasal, external ear canal, or rectal area dressing.

Figure 8:
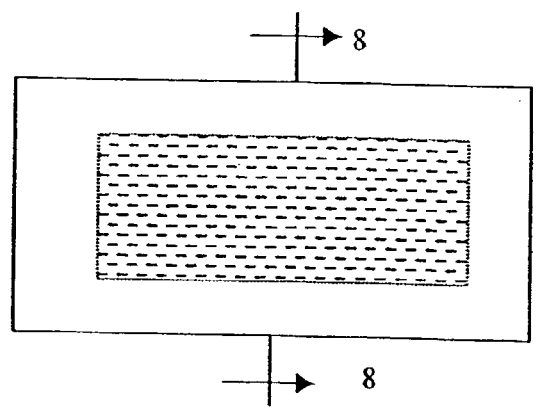
FIG. 8 is an illustration of one aspect of an island wound dressing.
Figure 9:
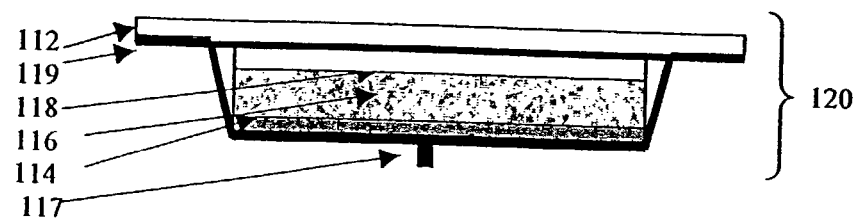
FIG. 9 is an illustration of a cross-section of FIG. 8.

Another wound dressing configuration is the island dressing. FIGS. 8, 9 and 13 demonstrate various representative aspects of island dressings. FIG. 8 shows the top view of a dressing with placement of the apertures (111) over the conducting layer (114), the absorbent layer (116), and the moisture regulation layer (118) but not in the peripheral area of an adhesive layer. The cross-section line 8-8 of FIG. 8 is shown in FIG. 9. A release liner layer (117) extends the entire surface of an adhesive layer (119) on the moisture regulation layer (118). The release liner layer is removed prior to application of the island dressing to a wound surface. An adhesive layer (119) is laminated to a backing sheet (112), and may include pressure sensitive adhesives for securing the dressing over the wound.

FIG. 13 illustrates an example of a multi-layer wound dressing in an island configuration, (150) having the same laminar composition as the dressing (120) shown in FIG. 9, with the exception that conductive layer (125) has been added between the absorbent layer (126), and the moisture regulation layer (128). The conductive layer (125) has similar composition to conductive layer (124). Both can be composed of about 100% conductive metal plated fibers, woven, knitted or non woven. The moisture regulation layer (128) can be adjacent to a backing sheet (122), that can be coated with a pressure sensitive adhesive (129) on the surface that is facing the moisture regulation layer (128). The moisture regulation layer, both conductive layers, and the absorbent layer all have the same length and width, and are substantially of smaller dimensions than the backing sheet (122) and pressure sensitive adhesive layer (129). They are also centrally seated on the adhesive surface (129) and the backing sheet (122), leaving an edge of the adhesive layer exposed around the perimeter of the layers, thus providing an island dressing configuration adapted for securing the dressing to the skin. Apertures penetrate through the backing sheet (122), the adhesive layer (129), and the moisture regulation layer (128) over the area covered by the moisture regulation layer, both conductive layers and the absorbent layer, but not the perimeter area. A release liner layer (127) covers the entire perimeter of the adhesive layer (129) prior to use, in order to prevent premature, unwanted contact of the adhesive-bearing surface.

In another aspect of the invention, a secondary dressing (160), illustrated in FIG. 14, may be applied to any aspect of the wound dressings (110, 120, 130, and 150) of the present invention. The secondary dressing provides a source for liquids and medicants that can be added to the wound dressings in addition to, or in combination with, the manual application of fluids or medicants using devices such as a bulb syringe. The secondary dressing (160) is composed of a pressure adhesive layer (142), an absorbent layer (141) and a semipermeable backing layer (143). The dimensions of the secondary dressing correspond to the dimensions of the wound dressing.

The pressure sensitive adhesive layer (142) is continuous around the perimeter of the secondary dressing. The pressure sensitive adhesive layer secures the secondary dressing to the primary dressing over the area of the apertures. The secondary dressing can be easily changed and removed on an as needed basis without disturbing the healing of the wound. The adhesive may be any of the medical grade adhesives heretofore employed for application to the skin. The absorbent layer (141) may contain a mixture of conductive metal plated fibers and non-conductive fibers, all conductive metal fibers, or all non-conductive fibers. The moisture regulation layer (143) can be an impermeable synthetic film The secondary dressing may be releasably secured to the primary dressing, such that the secondary dressing may be removed and replaced without removing or disturbing the primary wound contact dressing, for example, when the secondary dressing becomes saturated with wound exudates. The secondary dressing can be designed for the removal of excessive wound exudates or for the addition of liquids and medicants.

In another aspect of the invention, a fabric comprising any of the various aspects having conductive layer, absorption layer and moisture regulation layer of the present invention, can be provided. After assembly of the layers, the layers are laminated into a fabric suitable for cutting and forming into various configurations of wound dressings or wound healing devices.

The present invention comprises wound dressings or devices, comprising, at least one conductive layer. The wound dressing can further comprise at least one absorbent layer or at least one moisture regulation layer comprising a plurality of apertures disposed in the moisture regulation layer or any combination of the layers. Apertures of the moisture regulation layer allow passage of materials ranging in size from no passage of materials, that is moisture regulation layers with no apertures, apertures that allow gases but not liquids to pass, to apertures that allow liquids and gases to pass, to apertures of a size sufficient for the passage of microbial or environmental contaminants. The dressings may comprise moisture regulation layers attached to at least one absorbent layer or at least one conductive layer. The conductive layer may comprise at least one fiber that is coated three dimensionally with a metal or a metal alloy. The metal is selected from copper, silver, gold, palladium, nickel, cobalt or a combination thereof or the metal is selected from an alloy of nickel and boron, cobalt and boron, palladium and boron, nickel and phosphorus, cobalt and phosphorus, palladium and phosphorus, or a combination thereof. The conductive layer may also comprise a polymeric foam coated three dimensionally with metal or a metal alloy. The conductive layer may comprise at least one fiber or foam having grooves or channels along the longitudinal axis of the fiber or foam for capillary movement of water, to store or trap substances, and to provide large active surface areas for a given denier per fiber or foam.

Embodiments of the wound dressings of the present invention at least one conductive layer comprising at least one conductive fiber comprising a three dimensional coating of a metal, and at least one non-conductive fiber, wherein the conductive fiber and nonconductive fiber are uniformly distributed throughout the layer. The nonconductive fibers of the present invention can be composed of natural polymers, synthetic polymers, alginates, chitosan, rayon, cotton, or other polymeric substrates. Polyurethane is a preferable material for conductive and nonconductive fibers and foams. Absorbent layers can comprise a plurality of layers wherein the ratio of conductive fibers to non-conductive fibers is constant in a given layer or varies from layer to layer. In an embodiment, the ratio of conductive fibers to non-conductive fibers increases as the absorbent layer is positioned in closer proximity to the wound. Alternatively, the absorbent layer comprises conductive fibers comprising a three dimensional coating of a metal, and non-conductive fibers, wherein the conductive fibers and nonconductive fibers are uniformly distributed throughout the layer. The same arrangement of fibers and foams can be found in embodiments of conductive layers. In the layers, the ratio of conductive fiber to non-conductive fiber is between about 1:100 to 1:0, or the ratio of conductive fiber to non-conductive fiber is between about 1:50 to 1:0, or the ratio of conductive fiber to non-conductive fiber is between about 1:25 to 1:0.

Embodiments of the present invention may comprise a magnetic field provided to the wound surface by the conductive layer. A dressing may further comprise an adhesive layer. The conductive layer may comprises a fiber or foam three dimensionally coated with a metal. The at least one moisture regulation layer may be positioned adjacent to at least one absorbent layer. The layers may be shaped as polymeric sheets, films, or foams. An embodiment of a dressing may have multiple layers of conductive and absorbent layers. The at least one absorbent layer may comprise a plurality of layers, each layer increasing in thickness as the proximity from the wound increases. Embodiments include dressings where the conductive layers and absorbent layers alternate. The dressings may be formed into a shape selected from a pad, a tampon, a tubular configuration, an island dressing, a strip dressing, or any combination thereof. The apertures of the dressings may a geometric shape having curved lines, straight lines, or a combination thereof.

In treatment of wounds and use of the dressings described herein, a secondary dressing may also be used. A secondary dressing for applying to a wound dressing comprising at least one absorbent layer, at least one semi-permeable backing layer and a pressure adhesive layer continuous around the perimeter of the backing layer. These and other similar embodiments are intended by the present invention.

The wound dressings of the present invention are advantageous over the prior art because they do not require an external energy source or galvanic cell action to create and deliver silver ions. The dressings of the present invention can be formed into a number of different useful forms, depending on the particular application. In addition, the proper moisture environment at the treatment site can be created and regulated by controlling the amount of fluid at the wound site without disturbing the wound.

Methods of Use

Healthy human skin exhibits an electrical potential across the epithelium that is referred to as the transepithelial potential (TEP) or epidermal battery. The TEP is generated by an active ionic transfer system of sodium ions that enter the outer cells of the epithelium via specific channels in the outer membrane of these cells and migrate along a steep electrochemical gradient. The epidermal battery is generated through a series of electrogenic pumps that actively pump sodium ions, and tight gap junctions between epithelial cells that do not allow the reverse passage of the sodium ions. This results in the transport of sodium ions from the water bathing the epithelium cells to the internal body fluids of the animal, and causes the generation of a potential on the order of 10 mV to 70 mV across the epithelium.

It is believed that when a wound is made in the skin, an electric leak is produced that short-circuits the TEP allowing the voltage to reverse at the wound surface. With the disruption of the epithelium's electrogenic sodium transport mechanism within the wound, the TEP on the surface of the wound is significantly altered in the reverse direction. As one progresses laterally from the wound surface to normal tissue surrounding the wound, the potential across the skin increases, until a point is reached at which the potential across the skin is the full value normally found in unwounded skin. Thus a lateral voltage gradient is generated in the proximity of the wound margin as one transitions from wounded tissue to normal tissue. Various studies have reported that the lateral voltage gradient in experimental animals could be as high as 140 mV/mm. It has also been reported that within 24 hours after a wound is formed, the epidermally generated lateral voltage drops by 95%. Therefore, it is recognized that there is a lateral voltage gradient or "lateral potential" in the epidermis close to the margin of a wound. The greatest epidermally generated lateral voltage is found in the region of highest tissue resistance. In the amphibian, the locus of the major lateral potential is at the high resistance space between the epidermis and the dermis. In the mammal, the locus of the major lateral potential is at the space between the living and the dead cornified layers of epithelium.

While not wishing to be bound to any particular theory, the role of TEP in wound healing is explained in reference to FIG. 1 which demonstrates a cross-sectional representation of typical mammalian skin (5) with an electrical circuit generated by the TEP overlayed on the skin anatomy. The epidermis (7) overlies the dermis (9) at junction (11) and includes the stratum corneum layer (13) and the stratum spinosum layer (15) with a junction (17) there between. The stratum corneum layer is composed of dead cornified squamous epithelium. The wound (19) is filled with both cellular and dissolved elements of the blood including fibrinogen, fibronectin, polymorphonuclear leukocytes, platelets and red blood cells. Depending upon the location on the body (24) the surface (21) of the skin distal to the wound (19) can be expected to have a potential in a range of from about −10 to about −70 milivolts due to the TEP. The resistance of the return paths of current that is induced by a phenomenon known as an epidermal battery (29) is represented by resistors (25). The resistance of the wound is represented at (27). A dressing (120) in accordance with the present invention and having a highly conductive layer (114), absorbent layer (116), semipermeable layer (118), adhesive layer (119) and backing sheet layer (112), is shown proximate to the wounded skin surface (21). Prior to placement of the dressing on the wound, the wound potential (23) is more positive than on the surface of the skin (21), utilizing the surface potential to become less negative and, in certain instances, become positive. While not wishing to be bound to any particular theory, it is believed that this is be due to the removal of the epidermal battery (29) at the wound (19). The further the potential test point (23) is from the unwounded surface (21), the more closely the potential will approximate the potential of the positive side of the battery (29). If the wound is wet and therefore conductive, a wound current between points (31) and (33) will be induced by the TEP. The wound current will pass through the exudates and debris filling the wound (19) along the most efficient or lowest resistance path available. This is most likely proximate to the edge of the wound, because this will be the shortest path and the most moist path available. The wound current will pass from point (31) through the resistance at the junction (11) represented by resistor (35), into the wound at point (37), through the wound resistance (27) to point (39), where it re-enters the epidermis (7) at the junction (17), through the resistance of junction (17), represented as resistor (25), to point (33) on the other side of epidermal battery (29).

While not wishing to be bound by any particular theory, it is believed that when the dressing (120) is placed on the wound (19), the conductive layer (114) lowers the electrical potential of the wound, (e.g., at 23) by virtue of electrical contact with uninjured skin surfaces (21) which have a negative potential established by the epidermal battery (29). The dressing (120) lowers the potential of the wound surface and provides a conductive bridge between healthy skin surfaces (21) on either side of the wound (19). The point of maximum resistance shifts from point (39) to point (37). This in turn shifts the point of maximum lateral potential drop from point (39) to point (37). With the shift in lateral potential, the electrical characteristics of the wound more closely resemble the amphibian wound than the mammalian wound. Amphibian wounds are known to heal significantly faster than mammalian wounds because of this shift. Wound healing is enhanced and accelerated by the shift caused by the highly conductive surface of the wound dressing of the present invention. The shift in lateral potential from point (39) to point (37) can reduce the amount of stimulation that superficial nerve endings receive, thereby aiding in creating an analgesic effect. It is believed that the moisture level of the dressing (120) augments the restoration of the negative TEP and assists with the shift in lateral potential to deeper structures.

Figure 2:
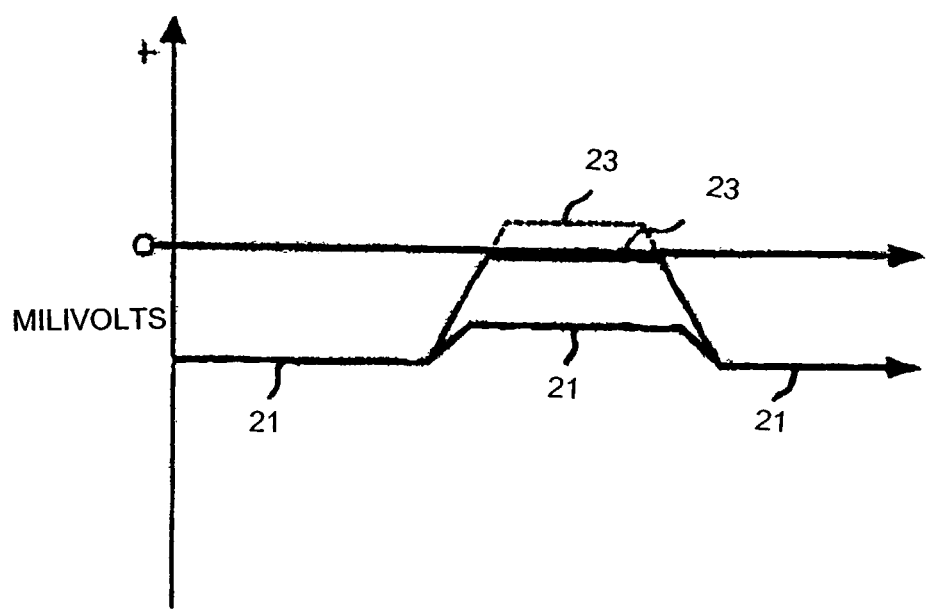
FIG. 2 is a graph of voltage verses position on the wounded skin as shown in FIG. 1.

FIG. 2 is a representative graph of the voltage at the surface of human skin as one proceeds from normal skin (21) to the open wound (23) to normal skin again. The area of normal skin (21) measures a relatively constant negative voltage between about 10 and about 70 milivolts. It is believed that the area of the wound surface where the TEP and the epidermal battery are disrupted (23) is always more positive than uninjured skin (21), reaching voltages between (23') and (23). When a dressing (110) in accordance with the present invention is applied and the wound is kept moist, it is possible to return to more normal skin potentials as shown at (21').

It is believed that the dressings of the present invention can contribute to expedited healing of the wound and aid in providing relief from the pain associated with wounds. Without wishing to be bound by any particular theory, the principle mechanisms of action that may account for the pain relieving aspects of the dressing of the present invention can be derived from the conductive layers of the dressing. First, the silver can create an antibacterial environment, which in turn can diminish the inflammation caused by the bacteria and subsequently can diminish pain. And second, the effect of a highly conductive layer can have a positive effect on the electrical field environment of the wound to be healed.

The present invention comprises methods of treating a wound in a human or an animal comprising, a) applying a dressing to a wound on a human or animal wherein the dressing comprises at least one conductive layer; at least one absorbent layer; and at least one moisture regulation layer comprising a plurality of apertures disposed in the moisture regulation layer; b) monitoring the absorbent layer of the dressing to determine a variation from a predetermined fluid level; and c) adding or removing fluid through the moisture regulation layer to maintain the predetermined fluid level. Methods can further comprise affixing a secondary dressing to the external surface of the dressing applied in step a) to the wound, wherein the secondary dressing comprises at least one absorbent layer, at least one semi-permeable backing layer and a pressure adhesive layer continuous around the perimeter of the backing layer.

In another aspect of the invention, the wound dressings can be used to regulate the moisture level of a wound of a human or animal. Many dressings are available that attempt to control the moisture level of wounds. Moisture retention is a term that refers to the ability of a dressing to consistently retain moisture at the wound site by interfering with the natural loss of moisture vapor due to evaporation. Semi-occlusive and occlusive wound dressings, such as films, foams, hydrogels and hydrocolloids, can be used to keep a wound moist by catching and retaining moisture vapor that is being lost by the wound. Normal skin has a moisture vapor transfer rate (MVTR), also called a transdermal water loss (TWL), of 43.2 grams/meter$^2$/24 hours. Many film dressings have MVTRs ranging from 400 to 2000 grams/meter$^2$/24 hours. Superficial wounds such as tape-stripped skin have an initial MVTR of 7,874 grams/meter$^2$/24 hours. In general, if a dressing material transmits less moisture vapor than the wound loses, then the wound will remain moist. When wound drainage levels are high, simple transmission of vapor will not dissipate adequate moisture to maintain physiologic tissue hydration. If the moisture vapor transmitted by a dressing is significantly less than the moisture being lost by the wound in vapor and liquid form, then drainage accumulates and remains in contact with the wound and surrounding skin. To maintain high drainage levels, a dressing must also have a liquid absorptive capacity in addition to vapor transmission ability. The process of absorption physically moves drainage away from the wound's surface and edges and into the dressing material. At the other end of the hydration spectrum, wound tissue that is already dry may need to be actively re-hydrated using dressing materials that donate water to the tissue or by removing the dressing and manually applying fluids to the wound.

One of the embodiments of the present invention allows for the addition or removal of fluid from the wound without removing the dressing. This control of fluid can be extremely important in trauma or battlefield situations where fluids need to be provided quickly. Additionally, the presence of the metal ions, provided by the conductive fibers or foams, aids in control of microbial contamination and thus, non-sterile fluids can be used. The moisture level of the wound can be regulated in comparison to some pre-determined level of moisture that can be beneficial. Advantageously, an indicator can be added to the wound dressing to indicate moisture level, electrical potential, metallic ion concentration, or pH.

To treat wounds, of an animal or human, the appropriate aspect of the wound dressing is selected and positioned on the wound, with the conductive layer in contact with the wound. The absorbent layer of the dressing is observed for variation of a moisture level that has been predetermined to be advantageous. Moisture, fluids, and medicants can be added to the wound dressing as needed through the moisture regulation layer. Moisture in excess of the predetermined level can also be removed through the moisture regulation layer. Alternatively, the moisture regulation layer can be removed and replaced with a new moisture regulation layer without disturbing the healing wound. Means to add and remove moisture include, but are not limited to, sponges, suction bulbs, syringes, gauze pads and the like.

In another aspect of the invention, a secondary dressing comprising at least one absorbent layer, at least one semi-permeable backing layer, and a pressure adhesion layer can be affixed to the external surface of the wound dressing. The secondary dressing can comprise liquids and/or medicants for treating the wound. The secondary dressing can be removed and replaced as needed to encourage continued healing of the wound.

In another aspect of the invention, the wound dressing can be placed internally to treat an organ or internal surgical incision. The dressing can be in the form of a gauze pad, packing material, fibrous dam, or any means to convey the treatment of the wound.

The wound dressing, when saturated and overlapping normal skin, may allow for controlled maceration of the surrounding uninjured skin. It is currently believed that the maceration of normal skin should be avoided. Maceration of normal skin is known to cause a breakdown of the cornified epithelium with subsequent loss of the anti-microbial barrier function of the skin. The reduction of the anti-microbial barrier function of the cornified epithelium is believed to result in an increased risk of microbial contamination at the wound surface. In an effort to control and prevent skin maceration, wound dressing designers have constructed wound dressings with special features that reduce the occurrence of maceration. Without wishing to be bound, the present invention has unexpectedly determined that the occurrence of maceration of normal skin surrounding a wound under the wound dressing of the present invention has not resulted in increased bioburden and/or contamination of the wound surface. While not wishing to be bound to any particular theory, the present invention has determined that the maceration of normal skin surrounding a wound being treated by the present invention has altered the local electrodynamic characteristics and resulted in an enhancement of the wound healing process.

It has been observed that regulating the moisture in and around the metal-plated fibers of the wound dressings of the present invention may facilitate the release of metallic ions from the surface of the metal because the passive release of metal ions can only take place within a liquid medium. Therefore, it is advantageous to keep the wound dressing moist in order to provide the effect of the metal plated fibers. Wounds that generate fluid exudates will usually provide the needed moisture required to activate the release of metal ions from the metallic surface.

Methods of Making

The preferred method of plating a metal on a fiber or foam for the conductive layer of the present invention is autocatalytically plating because it coats the fiber or foam uniformly with a three dimensional coating. This provides the maximum available surface area for accessible metal ions. In general, the fiber or foam has a nitrogen group. If the material from which the fiber or foam is made does not provide a nitrogen group on the surface, such nitrogens can be provided by added a layer of material or a coating that provides a nitrogen group on the surface. The present invention comprises use of materials that can be sensitized for autocatalytic metal plating. Such materials can be made into fibers, foams, films or other structures that function to provide the wound healing attributes of the devices described herein. For example, such materials include, but are not limited to, materials having nitrogen or silicon dioxide or other equivalently functional groups, that are capable of being sensitized. With, for example, the nitrogen group or silicon dioxide on the surface, the material can then be sensitized using methods known in the art. Once the material is sensitized, autocatalytic metal plating or coating of the material is performed.

The principle benefits of autocatalytically metal plating are: (1) uniform circumferential, three dimensional metal plating of the filament, foam, fiber, yarn or fabric; (2) large ratio of total metal surface area to geometric surface area; (3) high conductivity and low resistivity of the plated filaments, fibers, yarns and fabrics; (4) excellent adherence of the metallic coating to the non-conducting polymeric substrate with reduced risk of the metal coating flaking or fracturing off the non-conducting substrate; (5) excellent flexibility, conformability and elastomeric qualities; and (6) no limitations on filament, fiber, yarn or fabric design and construction.

Autocatalytic plating describes the method of depositing metals or metal alloys on non-conductive substrates by means of reduction-oxidation chemical reactions. Unlike electroplating, autocatalytic plating does not apply an electrical current from an external source to a conductive material or substrate for the purpose of depositing metals on the surface of the substrate. If the substrate is non-conductive, electroplating is not possible. Pure metal elements such as copper, gold, nickel and silver as well as binary alloys of nickel, cobalt or palladium with phosphorus or boron can be plated onto non-conductive material or substrate by the autocatalytic plating process.

The autocatalytic plating baths are designed such that when a sensitized substrate is introduced into the plating bath, deposition of the metal begins in a slow and uniform manner on all surfaces of the substrate. Once the process is initiated, the plating solution will continue to plate because the deposited metal catalyzes its own plating, thus making the reaction autocatalytic.

The autocatalytic metal plating process is the plating process of choice for filaments, fibers, yarns and fabrics in the electro-static discharge, electromagnetic interference and radio frequency interference industries. Autocatalytic metal plating of non-conductive substrates is used because the process is known to be superior to the vacuum vapor deposition process, the sputter coating deposition process, including magnetron sputtering, and the ion-beam assisted deposition process because it provides greater conductivity and resistivity of the plated substrate. Unlike vacuum vapor deposition, the sputter coating deposition and the ion-beam deposition processes, filaments, fibers, yarns and fabrics (woven, knitted, and non-woven) that have been metal plated by the autocatalytic process result in three dimensional continuous conductive pathways, while retaining the physical properties of the base material. Vacuum vapor deposition and sputter coating are inferior because they plate substrates in two dimensions with subsequent shadows, lack uniformity of the plated metal coatings, and alter the flexibility and conformability of the substrate. Vacuum vapor deposition and sputter coating typically plate substrates in a "line of sight" manner similar to commercial spray painting with compressed air.

Once the fibers are coated with a metal or metal alloy, they can be assembled into yarn, cord, thread, fabric, or combinations thereof, to form a layer of woven, knitted or non-woven fabric. The layers are assembled in any configuration predetermined by the intended aspect of the wound dressing. Autocatalytic silver plated fibers, filaments, yarns and fabrics are commercially available from Conductive Specialty Fabrics Manufacturing LLC, Lakemont, Ga.

The present invention comprises a method of manufacturing a dressing, wherein the dressing comprises at least one conductive layer; at least one absorbent layer; and at least one moisture regulation comprising a plurality of apertures disposed in the moisture regulation layer comprising, a) creating apertures in the moisture regulation layer, b) providing the conductive layer and the absorbent layer, c) assembling the absorbent layer, the moisture regulation layer and the conductive layer each on top of the other to form a contiguous fabric, and d) laminating the fabric of step c. The lamination step is performed by methods known in the art, including but not limited to, pressure sensitive adhesives, heat pressure lamination, flame lamination, hot melt lamination, point embossing, point bonding, spot bonding, sewing, or a combination thereof. The present invention also comprises a method of manufacturing a dressing, wherein the dressing comprises at least one conductive layer, at least one absorbent layer; and at least one moisture regulation layer positioned adjacent the absorbent layer or adjacent the conductive layer and comprising a plurality of varying sized apertures disposed in the moisture regulation layer, a) providing the conductive layer, the moisture regulation layer, and the absorbent layer, b) assembling the absorbent layer between the moisture regulation layer and the conductive layer, c) laminating the fabric of step b, and d) creating apertures in the moisture regulation layer. Creating apertures comprises making the appropriately sized and shaped apertures in the moisture regulation layer using whatever means will create the aperture. Cutting, piercing, premolding the fabric to include the apertures and similar actions are intended by the term creating apertures. Lamination is performed by pressure sensitive adhesives, heat pressure lamination, flame lamination, hot melt lamination, point embossing, point bonding, spot bonding, sewing, or a combination thereof.

The assembled layers of the woven, knitted or non-woven fabric of the present invention can be laminated by any manufacturing method known in the art for assembling layers of 100% conductive metallized fibers, layers of varying ratios of conductive metallized fibers to non-conductive fibers, layers of absorbent material, semi-permeable or impermeable film or foam, and backing sheets with pressure sensitive adhesives. Such methods can include, but are not limited to, heat pressure lamination, flame lamination, hot melt lamination or any combination thereof. Apertures can be cut in the moisture regulation layer prior to assembly of the layers, or alternatively, after the layers are laminated, using any manufacturing methods known in the art. The preferable method for placement of the apertures in the moisture regulation layer or the laminate of the moisture regulation layer, skin adhesive and backing sheet is to cut the apertures after the layers are laminated. Advantageously, a kiss cut method with a rotary cutting edge dye can be used to cut through only the moisture regulation layer or laminate of the moisture regulation layer, skin adhesive layer and backing sheet without disturbing the absorbency pad or wound contact layers. Alternatively, the moisture regulation layer or laminate of the moisture regulation layer, skin adhesive layer and backing sheet can be cut prior to lamination of the fabric, or the moisture regulation layer can be cut prior to assembly of the dressing.

One means for laminating and electrically integrating the layers is by point embossing or point bonding achieved by passing the fabric between a pair of niprolls, one roll having a series of spaced pins extending radially from the roll, and the other roll being flat. As the fabric layers are passed between the niprolls, the pins press into the fabric and force the fibers of one layer into the interstices of the next layer, thus bonding the two layers by fiber-to-fiber interaction forces. Alternatively, the layers can be laminated by adhesives, spot bonded (by ultrasonic welding or laser welding) or other techniques known to those skilled in the art. An alternative technique for laminating the layers is by sewing them together with conductive thread, preferably autocatalytic silver nylon plated poly or monofilament silver nylon thread. The conductive laminating thread enhances the overall conductivity of the conductive layer 114 and minimizes the resistance.

The wound dressings of this invention are most suitable when sterile. Preferably the dressings of this invention are provided sealed within a microbe-proof package. The dressing may be rendered sterile, for example, by gamma radiation. Surprisingly, it has been determined that the silver ion release concentration in aqueous solutions is improved with gamma radiation.

With respect to prior art, the application of metallic and ionic silver in the construction of wound dressings has focused on the anti-microbial aspects of silver and silver ions. The ability of the metallic surface to release particles of metallic silver or silver ions was related to the anti-microbial aspect of the dressing. The volume resistivity and conductivity was not addressed. In the present invention, resistivity and conductivity contribute to the capabilities of the wound dressing.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

A dressing of the present invention was used to treat a 45 year old male suffering from cutaneous manifestation of "shingles", *Herpes zoster* virus unilaterally at the tenth thoracic dermatome measuring 2 inches by 3 inches. The patient applied the multilayer wound pad illustrated in FIG. 4 after moistening the pad with tap water. The dressing was held in place with an adhesive layer and backing sheet Within five minutes, the patient reported 25% reduction in pain and within 2 hours nearly 90% reduction in pain. The patient reported that as the dressing dried out the pain returned, but never returned to the level experienced prior to placement of the dressing. When the dressing was re-moistened with water, the pain level was significantly reduced within ten minutes. The dressing was moistened through the moisture regulation layer without removing the dressing from the cutaneous viral outbreaks. The cutaneous lesions healed within 36 hours after application.

Example 2

A three year old female received 80% total body surface area full thickness (third degree burns) burns secondary to a flame injury. She was taken to surgery shortly after admission and all body surface areas were debrided of necrotic tissue. Integra® synthetic skin was applied and covered with the wound dressing illustrated in FIG. 4. The dressing was changed every two days leaving the synthetic skin in place. Gradually the synthetic skin was surgically excised and meshed split thickness skin grafts were applied. The wound dressing was applied over the meshed split thickness skin grafts, and was changed every two days until the wounds healed. The dressing was moistened every 12 hours with sterile water throughout the course of healing.

Example 3

Figure 4:
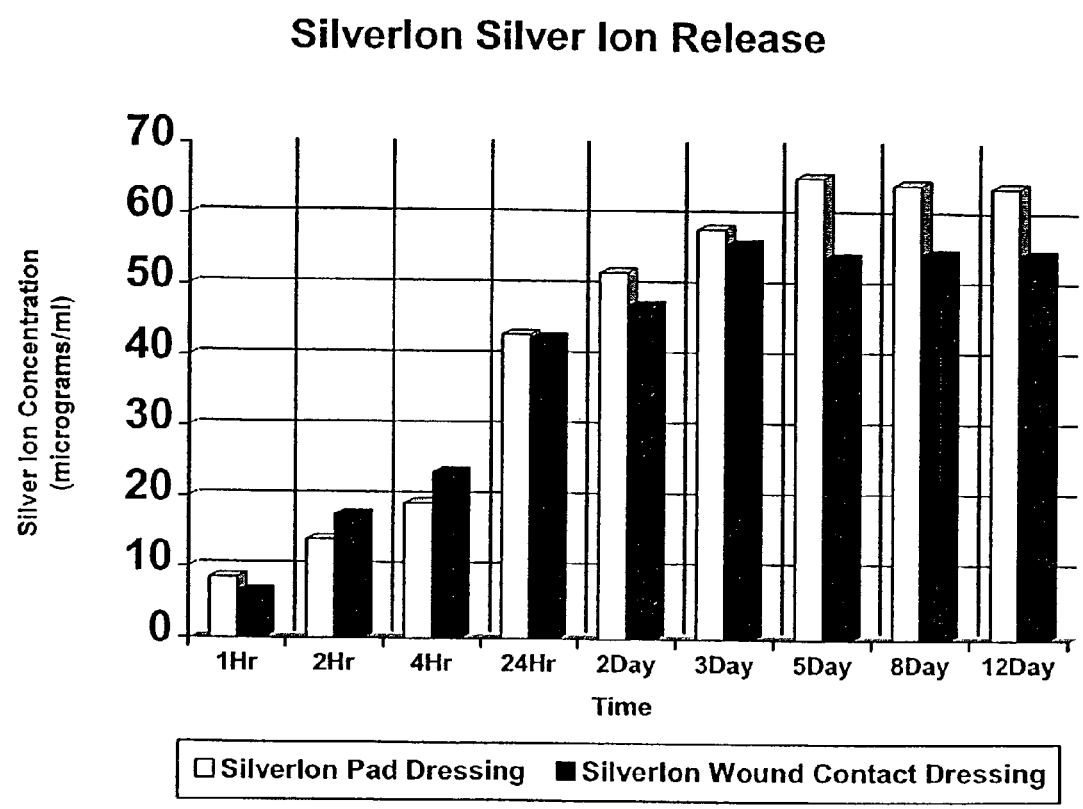
FIG. 4 is a graphic representation of the ionic silver release concentration from an autocatalytically silver plated fabric measured by inductively coupled plasma spectroscopy.

Table 1 illustrates the release of silver ions. A four inch by four inch square of an autocatalytic electroless silver plated 5.5 ounce per square yard warp knit fabric was incubated in tryptic soy broth at 37° C. The concentration of silver ions was measured by inductively coupled plasma spectroscopy over a twelve day period. FIG. 4 illustrates that the concentration of silver ions increased from less than 10 micrograms/ml the first hour, to over 60 micrograms/ml by day 5. Table 1

| Dressing | Time | | | | | | | | |
|---|---|---|---|---|---|---|---|---|---|
| | 1 Hr | 2 Hr | 4 Hr | 24 Hr | 2 Day | 3 Day | 5 Day | 8 Day | 12 Day |
| 4 inch by 4 inch 5.5 oz/yd$^2$ | 8.5 µg/ml | 13.9 µg/ml | 19.1 µg/ml | 43.1 µg/ml | 51.9 µg/ml | 58.1 µg/ml | 65.4 µg/ml | 64.5 µg/ml | 64.2 µg/ml |

It is well known that between 3 and 25 micrograms/milliliter of ionic silver are required to kill the most common pathologic wound microorganisms. Results indicated that the effective silver ion concentration was attained in about 1 to about 4 hours.

Example 4

Figure 5:
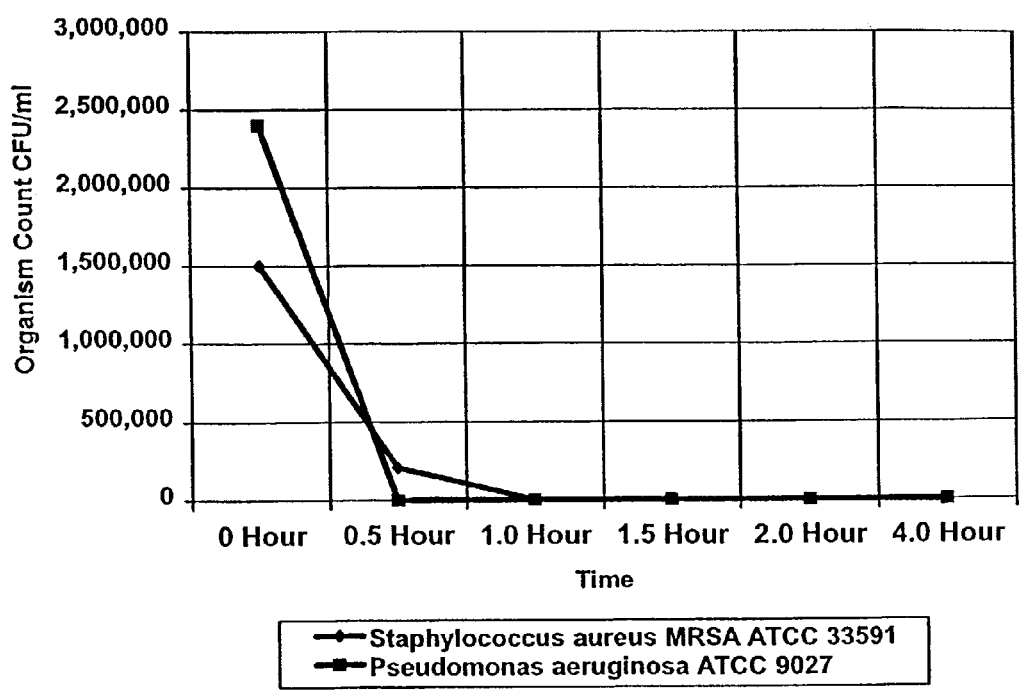
FIG. 5 is a graphic representation of the anti-microbial activity of an autocatalytically silver plated fabric.

FIG. 5 and Table 2 demonstrate the anti-microbial activity of a four inch by four inch sample of autocatalytically silver plated 5.5 ounce per square yard warp knit fabric. The fabric was positioned on media that was inoculated with pathogenic organisms *Pseudomonas aeuroginosa* and *Staphylococcus aureus* and incubated at 37° C. Growth of the organisms were measured by the "ASTM Standard Test Method for Determining the Anti-microbial Activity of Immobilized Anti-microbial Agents Under Dynamic Contact Conditions" ASTM E 2149-01. The reduction in CFU/ml from $10^6$ CFU/ml of *Pseudomonas aeuroginosa* ATCC 9027 and *Staphylococcus aureus* (MRSA) ATCC 33591 was studied. The reduction in organism counts expressed in colony forming units (CFU) per milliliter was measured at 0 hours, ½ hour, 1 hour, 1½ hour, 2 hours and 4 hours.

TABLE 2

| Bacterial Species | Time | | | | | |
|---|---|---|---|---|---|---|
| | 0 Hour | 0.5 Hour | 1.0 Hour | 1.5 Hour | 2.0 Hour | 4.0 Hour |
| *Staphylococcus aureus* MRSA ATCC 33591 | 1,500,000 CFU/ml | 210,000 CFU/ml | 3,400 CFU/ml | 2,500 CFU/ml | 120 CFU/ml | 0 |
| *Pseudomonas aeruginosa* ATCC 9027 | 2,400,000 CFU/ml | 0 CFU/ml | 0 CFU/ml | 0 CFU/ml | 0 CFU/ml | 0 CFU/ml |

Example 5

A study was conducted to determine the efficacy of a wound dressing of the present invention when used with Integra®, an artificial skin used for burn treatment.

A wound dressing was constructed comprising autocatalytic plated silver fibers for the conductive layer, and one layer of absorbent material was positioned between the conductive layer and the moisture regulation layer. The moisture regulation layer was constructed of a polyurethane film with 5 mm slit-shaped apertures cut into the layer.

The Integra® was prepared according to the manufacturer's directions to remove the EtOH preservative, and was cut into squares of 1.5 inches. Ten squares were used to test *Staphylococcus aureus* and ten squares were used for *Pseudomonas aeruginosa*. A seam was created in each square to simulate two pieces of Integra® being joined together to cover a wound. Each Integra® piece was centered on an individual standard blood agar plate. Each piece of Integra® was completely covered with a 2 inch square piece of wound dressing of the present invention and incubated at 37° C. for 24 hours. At 24 hours, two drops (≈100 microliters) of a suspension containing greater than $10^5$, colony forming units per milliliter of *Pseudomonas aeruginosa* or *Staphylococcus aureus* were added to the center of each dressing, simulating contamination in the post-operative patient. The dressings were re-moistened and incubated for 48 hours. After 48 hours, the dressings and the Integra® were carefully removed using sterile technique. Cultures were obtained from the area of the plate that was once covered with Integra, being sure to swab across the area where the seam in the product had been. Fresh agar plates were streaked with these samples and incubated for 24 hours.

The results are noted in the chart below.

| | *Staphylococcus aureus* (MRSA). | | *Pseudomonas aeruginosa* | |
|---|---|---|---|---|
| Time | +growth | −growth | +growth | −growth |
| 72 Hr | 6 plates | 4 plates | 3 plates | 7 plates |

The results illustrated that, when used in conjunction with Integra® artificial skin, the wound dressing of the present invention was 70% effective in preventing growth of *Pseudomonas aeruginosa* and 40% effective in preventing growth of *Staphylococcus aureus*.

Example 6

A test was conducted to determine the anti-microbial efficacy of a wound dressing of the present invention in an in vitro setting. Blood agar plates streaked with broth containing $10^6$ CFU per milliliter of *Pseudomonas aeruginosa* and Methicillin Resistant *Staphylococcus aureus* (MRSA) were tested.

A wound dressing of the present invention was constructed comprising autocatalytically plated silver fibers for the conductive layer, and one layer of absorbent material was positioned between the conductive layer and the moisture regulation layer. The moisture regulation layer was constructed of a polyurethane film with 5 mm slit-shaped apertures cut into the layer.

Ten blood agar plates were streaked with broth containing 106 CFU of *Pseudomonas aeruginosa* and ten blood agar plates were streaked with broth containing 106 CFU of Methicillin Resistant *Staphylococcus aureus* (MRSA). One inch square of the wound dressing of the present invention was placed in the center of each of ten blood agar plates. The remaining five plates were used as controls. The plates were incubated at 37° C. and sterile water added as needed to maintain moist dressings. After 72 hours, a culture was obtained from under each dressing and plated on blood agar. These plates were then incubated for 24 hours and evaluated for bacterial growth. This process was repeated after six days.

The results of bacterial growth were counted and recorded in the table below.

|  | *Staphylococcus aureus* (MRSA). | | *Pseudomonas aeruginosa* | |
| --- | --- | --- | --- | --- |
| Time | +growth | −growth | +growth | −growth |
| 72 Hr | 4 plates | 4 plates | 4 plates | 4 plates |
| 6 Days | 0 plates | 5 plates | 0 plates | 5 plates |

The conclusion was that the wound dressing was effective in killing Methicillin Resistant *Staphylococcus aureus* (MRSA) and *Pseudomonas aeruginosa*. Prolonged exposure to established bacterial growth resulted in progressive death.

Although the invention has been described in detail for the purpose of the illustration, it is understood that such detail is solely for that purpose, and variations can be made therein by those skilled in the art without departing from the spirit and scope of the invention, which is defined by the following claims.

What is claimed is:

1. A medical device, comprising:
   at least one non-adherent, permeable, conductive fabric having a surface resistance of about 10 ohms/in$^2$ to about 0.001 ohms/in$^2$, wherein the conductive fabric comprises synthetic polyamide fibers uniformly coated with metallic silver, wherein the coated polyamide fibers comprise multiple longitudinal filaments having a uniform three dimensional coating of metallic silver that provide large active surface areas for a given denier per fiber to passively deliver between 3 and 25 micrograms/ml of ionic silver to a wound in about 1 hour to promote or accelerate wound healing;
   optionally at least one absorbent layer; and
   optionally at least one moisture regulation layer comprising a plurality of apertures disposed in the moisture regulation layer, wherein the non-adherent conductive fabric contacts the surface of a wound when the medical device is applied to the wound.

2. The device of claim 1, wherein apertures of the moisture regulation layer allow passage of materials ranging in size from no passage of materials to passage of microbial or environmental contaminants.

3. The device of claim 1, wherein the moisture regulation layer is attached to the at least one absorbent layer or the at least one conductive layer.

4. The device of claim 1, wherein the conductive fabric further comprises at least one non-conductive fiber.

5. The device of claim 4, where in the nonconductive fiber is composed of natural polymers, synthetic polymers, alginates, chitosan, rayon, cotton, polyurethane, or polymeric substrates.

6. The device of claim 1, further comprising an adhesive layer.

7. The device of claim 1, wherein the at least one absorbent layer comprises conductive fibers comprising a three dimensional coating of a metal, and non-conductive fibers, wherein the conductive fibers and nonconductive fibers are uniformly distributed throughout the layer.

8. The device of claim 7, where in the non-conductive fibers are composed of natural polymers, synthetic polymers, alginates, chitosan, rayon, cotton, or polymeric substrates.

9. The device of claim 7, comprising a ratio of conductive fiber to non-conductive fiber is between about 1:100 to 1:0.

10. The device of claim 7, further comprising at least one moisture regulation layer positioned adjacent to the at least one absorbent layer.

11. The device of claim 1, wherein the absorbent layer comprises polymeric sheets, films, or a foam.

12. The device of claim 11, wherein the moisture regulation layer has apertures.

13. The device of claim 11, wherein the moisture regulation layer does not have apertures.

14. The device of claim 1, further comprising multiple conductive or absorbent layers.

15. The device of claim 14, wherein the at least one absorbent layer comprises a plurality of layers, each layer increasing in thickness as the proximity from the wound increases.

16. The device of claim 14, wherein the conductive layers and absorbent layers alternate.

17. The device of claim 1 wherein the apertures comprise a geometric shape having curved lines, straight lines, or a combination thereof.

18. The device of claim 1 wherein the device is selected from the group consisting of a pad, a tampon, a tubular configuration, an island dressing, and a strip dressing.

19. The medical device of claim 1, wherein the synthetic polyimide fibers are uniformly coated with metallic silver by autocatalytic metal plating.

20. A medical device consisting of
    one non-adherent, permeable, conductive layer having a surface resistance of about 10 ohms/in$^2$ to about 0.001 ohms/in$^2$ comprising a synthetic foam with large active surface areas having a uniform three dimensional coating of metallic silver to passively deliver 3 to 25 micrograms/ml of ionic silver in about 1 hour to a wound to promote or accelerate wound healing.

21. The medical device of claim 20 wherein the foam comprises polyurethane.

* * * * *